(12) United States Patent
Jones et al.

(10) Patent No.: US 9,283,336 B2
(45) Date of Patent: Mar. 15, 2016

(54) DELIVERY DEVICE AND RELATED METHODS

(71) Applicant: Manta Devices, LLC, Roslindale, MA (US)

(72) Inventors: Andrew Jones, Rosindale, MA (US); Richard L. Miller, Needham, MA (US)

(73) Assignee: Manta Devices, LLC, Cambridge, MA (US)

( * ) Notice: Subject to any disclaimer, the term of this patent is extended or adjusted under 35 U.S.C. 154(b) by 652 days.

(21) Appl. No.: 13/622,122

(22) Filed: Sep. 18, 2012

(65) Prior Publication Data

US 2013/0061851 A1    Mar. 14, 2013

Related U.S. Application Data

(63) Continuation of application No. PCT/US2011/029013, filed on Mar. 18, 2011.

(60) Provisional application No. 61/315,722, filed on Mar. 19, 2010.

(51) Int. Cl.
*A61M 15/00* (2006.01)
*B65D 83/06* (2006.01)

(52) U.S. Cl.
CPC ....... *A61M 15/0028* (2013.01); *A61M 15/0035* (2014.02); *A61M 15/0038* (2014.02); *A61M 15/0045* (2013.01); *A61M 15/0048* (2014.02); *B65D 83/06* (2013.01); *A61M 2202/064* (2013.01); *A61M 2206/16* (2013.01)

(58) Field of Classification Search
CPC ...... A61M 15/0021; A61M 15/0028–15/0043; A61M 15/0061
See application file for complete search history.

(56) References Cited

U.S. PATENT DOCUMENTS 2,307,986 A    1/1943  Bolte et al.
2,860,638 A    11/1958 Bartolomeo
(Continued)

FOREIGN PATENT DOCUMENTS

DE    4400083 A1    7/1995
EP    0407276       1/1991
(Continued)

OTHER PUBLICATIONS

Partial International Search Report from related International Application No. PCT/US2008/008303 dated Dec. 4, 2008.
(Continued)

*Primary Examiner* — Valerie L Skorupa
(74) *Attorney, Agent, or Firm* — Grossman Tucker Perreault & Pfleger, PLLC

(57) ABSTRACT

A dose delivery device with a mouthpiece having an inlet, an outlet, and an air path extending between the inlet and the outlet. A dose chamber having an opening may hold a dose, e.g., for inhalation by a user. A disc element may be arranged to move between a closed position in which the disc element closes the opening of the dose chamber, and an open position in which the disc opens the dose chamber to permit introduction of the dose into the air path of the device. Movement of the disc element from the closed position to the open position may be in a direction away from the dose chamber (e.g., a puller may engage the disc element and pull the element away from the chamber) and may leave a substantial portion of the dose in the dose chamber.

16 Claims, 24 Drawing Sheets

(56) References Cited

U.S. PATENT DOCUMENTS

| | | | |
|---|---|---|---|
| 2,974,787 A | 3/1961 | Cooper | |
| 3,888,253 A | 6/1975 | Watt et al. | |
| 2,893,392 A | 6/1976 | Gerstel et al. | |
| 4,249,526 A | 2/1981 | Dean et al. | |
| 4,338,931 A | 7/1982 | Cavazza | |
| 4,601,896 A | 7/1986 | Nugent | |
| 5,035,237 A | 7/1991 | Newell et al. | |
| 5,167,242 A | 12/1992 | Turner et al. | |
| 5,239,993 A | 8/1993 | Evans | |
| 5,320,714 A | 6/1994 | Brendel | |
| 5,388,572 A | 2/1995 | Mulhauser et al. | |
| 5,394,868 A * | 3/1995 | Ambrosio et al. | 128/203.15 |
| 5,400,808 A | 3/1995 | Turner et al. | |
| 5,476,093 A | 12/1995 | Lankinen | |
| 5,501,236 A | 3/1996 | Hill et al. | |
| 5,562,918 A | 10/1996 | Stimpson | |
| 5,596,982 A | 1/1997 | Blaha-Schnabel | |
| 5,622,166 A * | 4/1997 | Eisele et al. | 128/203.12 |
| 5,647,349 A | 7/1997 | Ohki et al. | |
| 5,669,378 A | 9/1997 | Pera et al. | |
| 5,673,793 A | 10/1997 | Seidler | |
| 5,775,320 A | 7/1998 | Patton et al. | |
| 5,893,452 A | 4/1999 | De Nervo | |
| 5,921,237 A | 7/1999 | Eisele et al. | |
| 5,947,117 A | 9/1999 | Herold | |
| 5,954,204 A | 9/1999 | Grabowski | |
| 6,029,663 A | 2/2000 | Eisele et al. | |
| 6,065,472 A * | 5/2000 | Anderson et al. | 128/203.21 |
| 6,089,228 A | 7/2000 | Smith et al. | |
| 6,209,538 B1 | 4/2001 | Casper et al. | |
| 6,230,707 B1 | 5/2001 | Horlin | |
| 6,234,169 B1 | 5/2001 | Bulbrook et al. | |
| 6,328,034 B1 | 12/2001 | Eisele et al. | |
| 6,347,629 B1 | 2/2002 | Braithwaite | |
| 6,401,712 B1 | 6/2002 | Von Schuckmann | |
| 6,415,790 B1 * | 7/2002 | Leedom et al. | 128/203.15 |
| 6,427,688 B1 | 8/2002 | Ligotke et al. | |
| 6,443,152 B1 | 9/2002 | Lockhart et al. | |
| 6,443,307 B1 * | 9/2002 | Burridge | 206/532 |
| 6,461,322 B1 * | 10/2002 | Ritsche | 604/57 |
| 6,550,477 B1 | 4/2003 | Casper et al. | |
| 6,595,203 B1 | 7/2003 | Bird | |
| 6,595,210 B2 | 7/2003 | Ohki et al. | |
| 6,655,381 B2 | 12/2003 | Keane et al. | |
| 6,681,768 B2 | 1/2004 | Haaije de Boer et al. | |
| 6,748,947 B2 | 6/2004 | Keane et al. | |
| 6,810,872 B1 | 11/2004 | Ohki et al. | |
| 6,871,646 B2 | 3/2005 | Keane et al. | |
| 6,932,082 B2 | 8/2005 | Stein | |
| 6,941,947 B2 | 9/2005 | Young et al. | |
| 6,971,384 B2 | 12/2005 | Gieschen et al. | |
| 7,025,056 B2 | 4/2006 | Eason et al. | |
| 7,025,057 B2 | 4/2006 | Chawla | |
| 7,143,765 B2 | 12/2006 | Asking et al. | |
| 7,401,713 B2 | 7/2008 | Ede et al. | |
| 7,464,704 B2 * | 12/2008 | Braithwaite | 128/200.21 |
| 8,109,267 B2 | 2/2012 | Villax et al. | |
| 2001/0027790 A1 | 10/2001 | Gieschen et al. | |
| 2001/0029948 A1 | 10/2001 | Ingle et al. | |
| 2002/0006316 A1 | 1/2002 | Schuler et al. | |
| 2002/0020408 A1 | 2/2002 | Knauer | |
| 2002/0092523 A1 | 7/2002 | Connelly et al. | |
| 2002/0170560 A1 * | 11/2002 | Young et al. | 128/203.15 |
| 2003/0034271 A1 | 2/2003 | Burridge | |
| 2004/0107963 A1 | 6/2004 | Finlay et al. | |
| 2004/0168687 A1 | 9/2004 | Asking et al. | |
| 2004/0182387 A1 | 9/2004 | Steiner et al. | |
| 2004/0206350 A1 | 10/2004 | Alston et al. | |
| 2004/0211419 A1 | 10/2004 | Eason et al. | |
| 2004/0236282 A1 * | 11/2004 | Braithwaite | 604/158 |
| 2005/0022813 A1 | 2/2005 | Alston | |
| 2005/0188988 A1 | 9/2005 | Poole et al. | |
| 2006/0005833 A1 | 1/2006 | Gieschen et al. | |
| 2006/0108877 A1 | 5/2006 | Tegel | |
| 2006/0169278 A1 | 8/2006 | Djupesland et al. | |
| 2007/0023381 A1 * | 2/2007 | Cerveny | 215/228 |
| 2007/0074721 A1 | 4/2007 | Harmer et al. | |
| 2007/0151562 A1 | 7/2007 | Jones et al. | |
| 2007/0163574 A1 * | 7/2007 | Rohrschneider et al. | 128/200.19 |
| 2008/0127974 A1 * | 6/2008 | Lastow | 128/203.21 |
| 2008/0142009 A1 * | 6/2008 | Carrico et al. | 128/203.15 |
| 2008/0251072 A1 | 10/2008 | Lulla et al. | |
| 2008/0314384 A1 | 12/2008 | Harris et al. | |
| 2009/0013994 A1 | 1/2009 | Jones et al. | |
| 2009/0250057 A1 | 10/2009 | Wachtel | |
| 2009/0308392 A1 | 12/2009 | Smutney et al. | |
| 2009/0321295 A1 | 12/2009 | Ede et al. | |
| 2010/0132705 A1 * | 6/2010 | De Vos | 128/203.21 |

FOREIGN PATENT DOCUMENTS

| | | |
|---|---|---|
| EP | 1844809 A1 | 10/2007 |
| GB | 1211168 A | 11/1967 |
| GB | 2179260 A | 3/1987 |
| GB | 2375310 A | 11/2002 |
| GB | 2405798 A | 3/2005 |
| GB | 2420982 A | 6/2006 |
| JP | 08-103499 A | 4/1996 |
| WO | WO 90/07351 A1 | 7/1990 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 01/56640 A1 | 9/2001 |
| WO | WO 01/85097 | 11/2001 |
| WO | WO 02/098495 A1 | 12/2002 |
| WO | WO 03/000326 A1 | 1/2003 |
| WO | WO 03/015857 A1 | 2/2003 |
| WO | WO 2004/103446 A1 | 12/2004 |
| WO | WO 2005/002654 A3 | 1/2005 |
| WO | WO 2005/025656 A1 | 3/2005 |
| WO | WO 2005/030305 A1 | 4/2005 |
| WO | WO 2006/066910 A1 | 6/2006 |
| WO | WO 2007/007110 A1 | 1/2007 |
| WO | WO 2009/092650 | 7/2009 |

OTHER PUBLICATIONS

International Preliminary Report on Patentability from related International Application No. PCT/US2010/000090 dated Jul. 19, 2011.

* cited by examiner

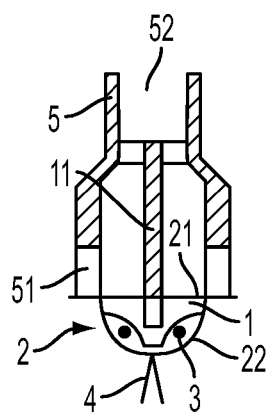
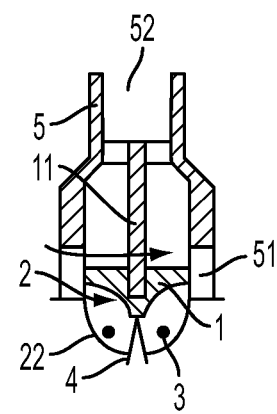
FIG. 1A          FIG. 1B
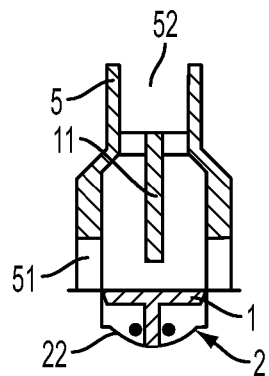
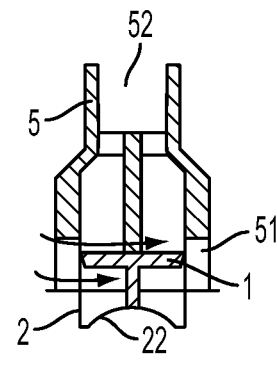
FIG. 2A          FIG. 2B
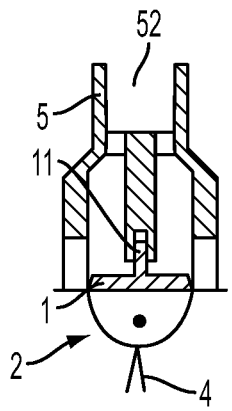
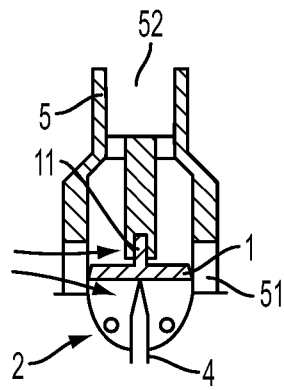
FIG. 3A          FIG. 3B

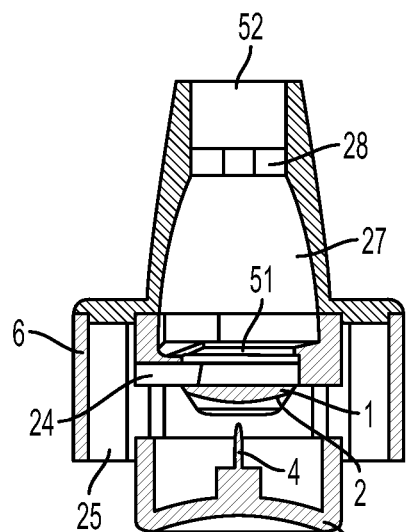
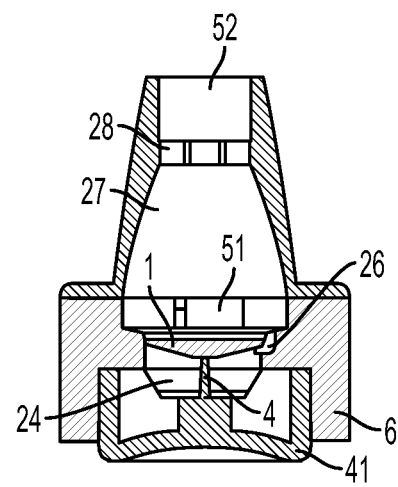
FIG. 5
FIG. 6
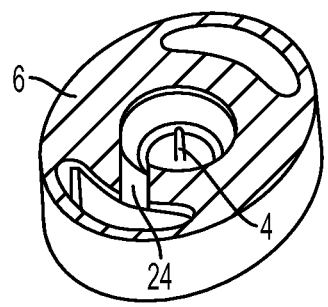
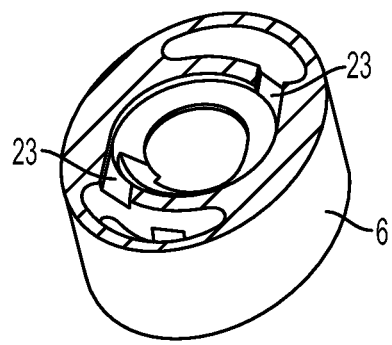
FIG. 7
FIG. 8

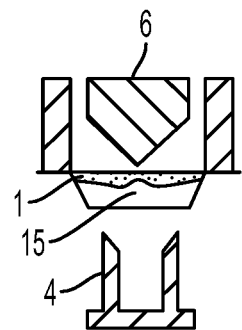
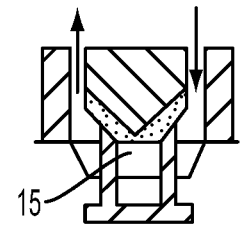
FIG. 29A    FIG. 29B
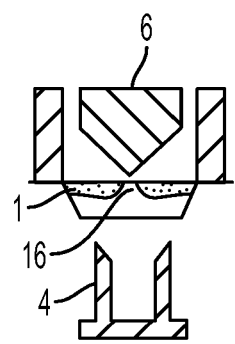
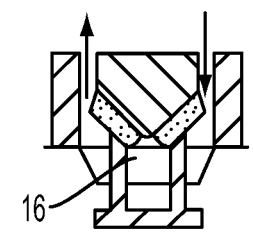
FIG. 30A    FIG. 30B
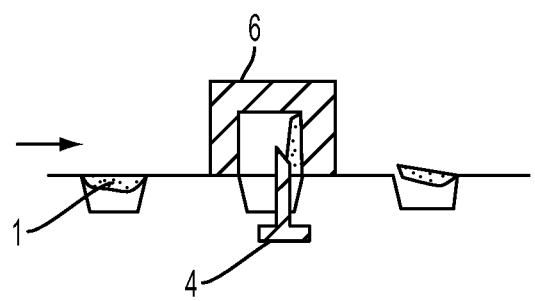
FIG. 30C

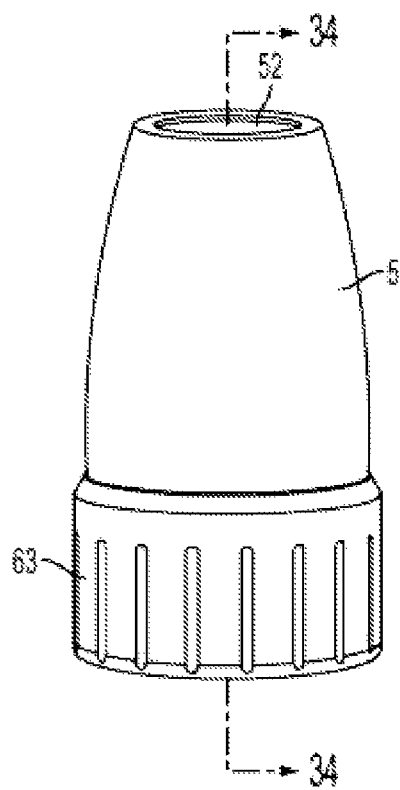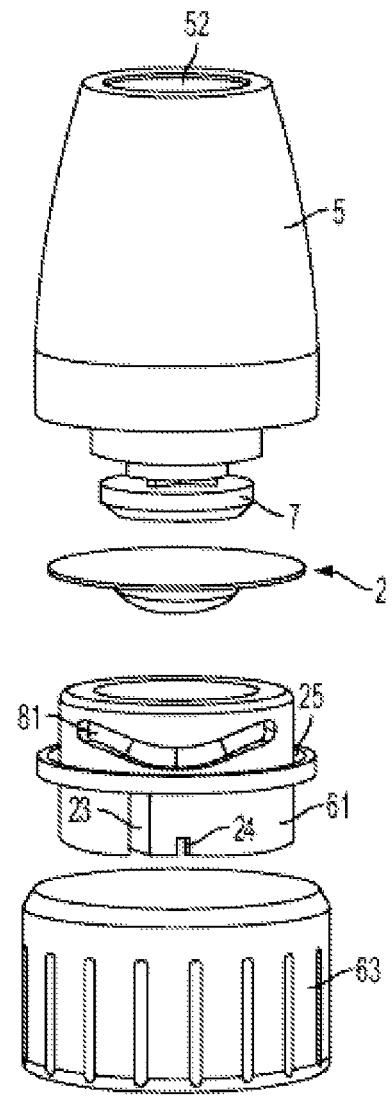
FIG. 32
FIG. 33

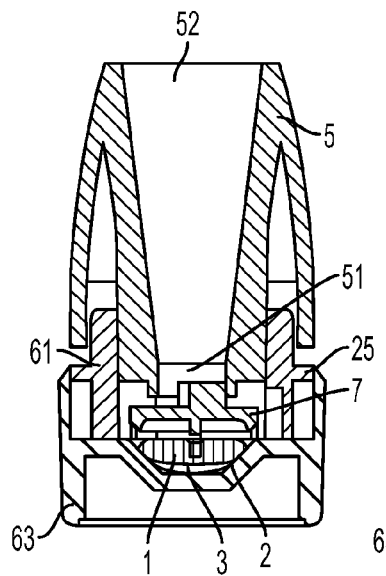
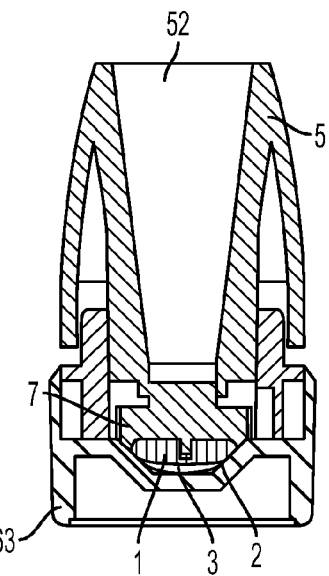
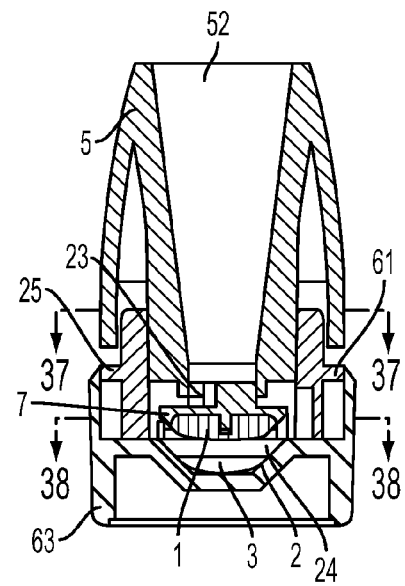
FIG. 34   FIG. 35   FIG. 36
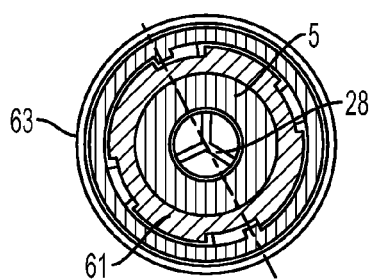
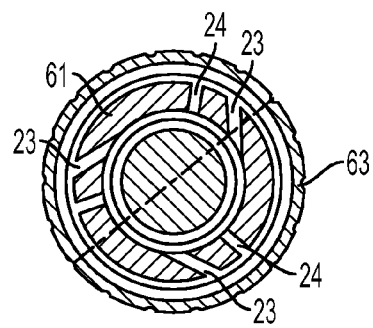
FIG. 37   FIG. 38

DELIVERY DEVICE AND RELATED METHODS

This application is a continuation of International patent application PCT/US2011/029013, filed Mar. 18, 2011, which claims the benefit of U.S. Provisional application No. 61/315,722, filed Mar. 19, 2010, both of which applications are hereby incorporated by reference in its entirety.

BACKGROUND

Medicament in the form of dry powder may be delivered directly into the lungs, such as by inhalation. Administering medicament in this manner may prove less invasive than other drug delivery techniques, such as hypodermic injections. Direct inhalation of medicament may also allow smaller doses to be used to achieve results similar to those of the same drug taken orally. Inhalation may also help avoid undesirable side effects associated with administering drugs orally or by injection.

SUMMARY OF INVENTION

Aspects of the invention relate to devices, systems, and methods that are used to deliver a dose of a powder, such as a medicament, a flavorant, or another substance. The devices, systems and methods may include features that allow the dose to be protected (e.g., from contamination and/or degradation) prior to use, and to be delivered in a metered manner. For example, in some embodiments, the dose is isolated to a selected volume/dose chamber by a barrier, such as a foil layer around the dose chamber or the entire delivery device that prevents the ingress of contaminants and/or the egress of a dose from dose chamber prior to use. A cutter, positioned either internally or externally of the dose chamber, maybe be moved by various mechanisms to rupture the barrier in a consistent manner or otherwise open the dose chamber. As a result, the initial location of the drug dose is known, and the dose may be delivered from the dose chamber through an opening that is formed consistently and predictably.

In one aspect of the invention, a dose delivery device includes a mouthpiece having an inlet at a first end, an outlet at a second end, and a mouthpiece air path extending between the inlet and the outlet. A dose chamber having an opening may be associated with the mouthpiece and hold a dose, e.g., for inhalation by a user. A disc element may be arranged to move between a closed position in which the disc element closes the opening of the dose chamber, and an open position in which the disc opens the dose chamber to permit introduction of the dose into the mouthpiece air path of the mouthpiece. In the closed position, the disc element, which may be substantially rigid and/or substantially flat, may be in contact with the dose, e.g., to maintain the dose in the dose chamber. The movement of the disc element from the closed position to the open position may be in a direction away from the dose chamber and may leave a substantial portion of the dose in the dose chamber, i.e., movement of the disc element may leave the dose largely undisturbed in the dose chamber.

In one embodiment, the delivery device may include a housing that receives the a portion of the mouthpiece such that the mouthpiece is movable relative to the housing. For example, the housing may have a recess that receives and surrounds the first end of the mouthpiece and engages with the mouthpiece so that the mouthpiece may be rotated relative to the housing and/or moved along an axis relative to the housing. In one arrangement, the disc element may be arranged to move from the closed position to the open position with movement of the mouthpiece relative to the housing. For example, the disc element may be fixed relative to the mouthpiece at the first end of the mouthpiece, and movement of the mouthpiece along an axis may lift the disc element from the dose chamber opening. Threaded engagement of the mouthpiece with the housing may allow the mouthpiece to be rotated relative to the housing so as to cause the mouthpiece to move along an axis relative to the housing. In one embodiment, the axis may extend in the same direction as the mouthpiece air path that extends from an inlet of the mouthpiece to an outlet of the mouthpiece. In some arrangements, the disc element moves along the axis when moving from the closed position to the open position. The disc element may have a top surface that is perpendicular to the axis during movement from the closed position to the open position. In one embodiment, the mouthpiece is movable along the axis toward the dose chamber to engage the mouthpiece with the disc element, and then movable along the axis away from the dose chamber to move the disc element from the closed to the open position. For example, the dose chamber may include a foil barrier layer that encloses the dose chamber and the disc element may be located inside of the foil barrier layer. Movement of the disc element away from the dose chamber may remove a portion of the foil barrier layer from the dose chamber, opening the chamber. In other embodiments, the dose chamber may not include a foil or other barrier layer, and may be closed by two mated, molded plastic parts. One of those parts may be the disc element.

The housing may include one or more passages that provide a pathway for air to pass to the mouthpiece inlet and/or the dose chamber. In one arrangement, the pathway may be at least partially arranged in a first direction, and the air path at the outlet of the mouthpiece may be arranged in a second direction that is transverse to the first direction, e.g., the first and second directions may be perpendicular to each other. The disc element may move in the second direction, i.e., the same direction as air flow at the mouthpiece outlet, when moving from the closed position to the open position. For example, the air path at the mouthpiece outlet may be arranged in a second direction that is perpendicular to a plane of the disc element. This arrangement can help prevent large particles of the dose from passing from the dose chamber to the outlet, and instead may help ensure that large particles are broken up before exiting the mouthpiece. Air that is introduced to the dose chamber may be arranged in a pathway that is in a plane that is parallel to a plane of the disc element (and perpendicular to the air flow at the mouthpiece outlet). The disc element may direct air from the one or more passages to flow into the dose chamber when the disc element is in the open position, e.g., to help introduce the dose into the air flow at the mouthpiece inlet.

In another aspect of the invention, a dose delivery device includes a mouthpiece having an inlet at a first end, an outlet at a second end, and a mouthpiece air path extending between the inlet and the outlet. A dose chamber for holding a dose and having an opening may be associated with the mouthpiece and a disc element may be arranged to move between a closed position and an open position in which the dose chamber is opened to permit introduction of the dose into the mouthpiece air path. A puller may be arranged to engage with the disc element while the disc element is in the closed position and move the disc element in a single direction from the closed position to the open position. For example, if the dose chamber includes a foil barrier layer that encloses the dose chamber and the disc element is located inside of the foil barrier layer, the puller may pierce the foil barrier layer to engage with the disc element, and then move the disc element in a single direction (e.g., away from the dose chamber) to open the dose chamber. (Movement of the disc element in a single direction may involve rotation as well as linear or other motion of the disc element.) The puller may include an edge that cuts a portion of the foil barrier layer near the disc element as the puller moves toward the disc element for engagement with the disc element. Alternately, the disc element may cut the foil barrier layer, either alone or in cooperation with another cutting edge or structure outside of the dose chamber.

In one embodiment, a housing may receive or otherwise engage a portion of the mouthpiece such that the mouthpiece is movable relative to the housing. The disc element may be arranged to move from the closed position to the open position with movement of the mouthpiece relative to the housing, e.g., rotation of the mouthpiece relative to the housing may cause the mouthpiece to move the disc element away from the dose chamber. The housing may include one or more passages that provide a pathway for air to pass to the mouthpiece inlet and/or the dose chamber, e.g., air may pass into the passage(s) to the dose chamber, and then to the mouthpiece inlet, or may pass directly from the passage to the mouthpiece inlet. The disc element may direct air from the one or more passages to flow into the dose chamber when the disc element is in the open position. For example, air flowing in the passage(s) may strike the disc element and be deflected into the dose chamber, causing a portion of the dose to be entrained in the air flow.

In another aspect of the invention, a dose delivery device includes a mouthpiece having an inlet at a first end, an outlet at a second end, and a mouthpiece air path extending between the inlet and the outlet. A housing may be attached to the mouthpiece such that the mouthpiece is movable relative to the housing. A dose chamber holding a dose and having an opening may be attached to the housing and a disc element may be arranged to move between a closed position and an open position in which the dose chamber is opened to permit introduction of the dose into the air path. Movement of the mouthpiece relative to the housing may cause the disc element to move from the closed position to the open position. For example, the disc element may be fixed relative to the mouthpiece so that as the mouthpiece moves relative to the housing, the disc element moves to open the dose chamber The housing may include one or more passages that provide a pathway for air to pass to the mouthpiece inlet and/or the dose chamber, and the pathway may be at least partially arranged in a first direction (or arranged in a plane) such that the air path at the mouthpiece outlet is arranged in a second direction that is transverse to the first direction (or the plane), e.g., the first and second directions may be perpendicular to each other. The housing may have a recess that threadedly engages the first end of the mouthpiece, e.g., so that rotation of the mouthpiece causes the mouthpiece to move axially relative to the housing.

Aspects of the invention can be used in any suitable arrangement, including dose delivery device that are usable a single time with a single dose chamber, and including a dose delivery device that is usable multiple times with multiple dose chambers. For example, dose delivery device may include a plurality of dose chambers arranged in a multi-dose chamber configuration in which each dose chamber can be serially opened and used to deliver a dose to a user.

Other aspects, features and advantages will be apparent from the description of the following embodiments and from the claims.

BRIEF DESCRIPTION OF THE DRAWINGS

Illustrative embodiments of the invention are more particularly described in the following detailed description, taken in conjunction with the accompanying drawings. In the drawings, like reference characters generally refer to the same parts throughout the different views. Also, the drawings are not necessarily to scale, emphasis instead generally being placed upon illustrating principles of the invention.

FIGS. 1a and 1b show a cross sectional view of a dose delivery device in which a cutter, in the form of a disc element, is guided in movement by structure of the device body;

FIGS. 2a and 2b show a cross sectional view of a dose delivery device in which the cutter, in the form of a disc element, is stopped in its opening movement by structure of the device body;

FIGS. 3a and 3b show a cross sectional view of a dose delivery device in which a cutter, in the form of a disc element, is located above a foil barrier layer of the dose chamber;

FIGS. 5 and 6 show cross sectional views of the FIG. 4 embodiment having first and second positions, respectively, of an actuation button;

FIGS. 7 and 8 show cross sectional views of the FIG. 4 embodiment along the lines 7-7 and 8-8 in FIG. 4;

FIG. 14d shows a cross sectional view of the FIG. 14a embodiment along the lines 14d-14d in FIG. 14a;

FIGS. 29a and 29b show an illustrative embodiment in which the cutter has a hinge;

FIGS. 30a and 30b show an illustrative embodiment in which the cutter has a gap;

FIG. 30c shows an embodiment in which the cutter is arranged to rotate about an axis located at an edge of the cutter;

FIG. 32 shows a front view of another illustrative embodiment of a dose delivery device;

FIG. 33 shows an exploded view of the FIG. 32 embodiment;

FIGS. 34-36 show cross sectional views along the line 34-34 in FIG. 32 with the mouthpiece in different positions;

FIG. 37 shows a cross sectional view along the line 37-37 in FIG. 36;

FIG. 38 shows a cross sectional view along the line 38-38 in FIG. 36;

DETAILED DESCRIPTION

Figure 4:
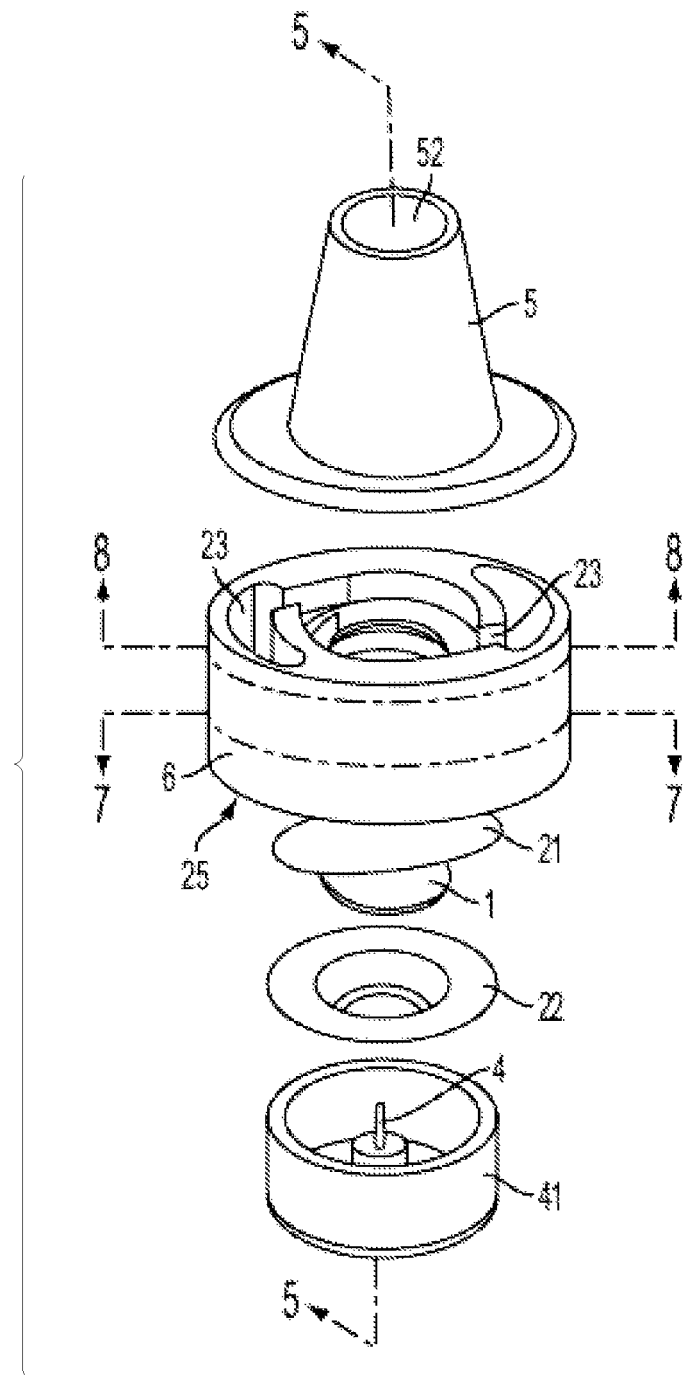
FIG. 4 shows an exploded view of a dose delivery device in another illustrative embodiment.

Delivery devices described herein include one or more dose chambers for storing and delivering a dose of a substance, such as a powdered medicament, including blended formulations, excipient formulations, neat formulations or combinations thereof, flavorant, to a subject. The dose chamber may be placed in fluid communication with an air pathway to ready the dose for delivery to the subject. Air is drawn or pushed through the air pathway and at least a portion of the air enters the dose chamber to entrain the dose in a metered manner. Air then reenters the air pathway from the dose chamber, laden with powder from the dose chamber, and moves towards an outlet of the delivery device to a subject.

According to some aspects, a cutter (such as a disc element) may be incorporated into the structure of a dose chamber. Movement of the cutter relative to the dose chamber may cause a rupturable portion of the barrier to open or the dose chamber to otherwise be opened, thereby providing a passageway into and/or out of the dose chamber. The dose chamber itself may be configured to deform in a manner that, when actuated by a user, causes the cutter to rupture the barrier. Additionally or alternatively, a punch, puller or other structure may pass through a portion of the dose chamber wall, then contact and move the cutter relative to the barrier, causing the cutter to rupture the barrier.

FIG. 1a shows a cutter 1 positioned inside of a dose chamber 2 adjacent to a rupturable foil layer 21 of a foil-on-foil dose chamber. A flat, upper foil layer 21 and a dish-shaped, lower foil layer 22 are adhered together to define the dose chamber 2 which contains a dose 3. A punch 4 lies adjacent to the dish-shaped foil layer. When moved, the punch 4 pierces or otherwise deforms the dish-shaped foil layer 22. The punch or deformed portion of the dish-shaped foil layer 22 contact the cutter 1 and then urge the cutter to move relative to the upper foil layer 21, as shown in FIG. 1b, to cause a rupture. Movement of the cutter 1 maybe guided by a post 11, or other structure, toward/through the barrier. This movement opens fluid communication between the dose chamber and an air pathway, such that air may enter the dose chamber 2 to entrain dose 3 for delivery therefrom. In this embodiment, the dose delivery device includes a mouthpiece 5 that has an inlet 51 and an outlet 52. An air path is established from the inlet 51 to the outlet 52 so that dose 3 entrained into air flowing in the air path can be carried to the outlet 52, e.g., for delivery to the mouth and lungs of a user. A lower portion of the cutter 1, which may be a disc element and which may be in contact with the dose 3, may be arranged to direct air flowing from the inlet 51 into the dose chamber 2.

According to other embodiments, movement of a portion of a wall of the dose chamber 2 itself may cause the cutter 1 to move and rupture a barrier of the dose chamber 2. FIGS. 2a and 2b show one such embodiment where a dish-shaped wall 22 of the dose chamber 2 flexes or snaps in a controlled manner when depressed to move a cutter through a rupturable barrier wall of the dose chamber 2. According to yet another embodiment, the structure of the dose chamber 2 may include a bellows or other flexible structure that moves when urged, and causes a cutter 1 to rupture a barrier of a dose chamber.

The cutter 1 may be positioned internal or external of a dose chamber, with respect to the barrier that the cutter 1 is configured to rupture. FIGS. 3*a* and 3*b* show one embodiment where the cutter 1 is positioned external to the dose chamber. As with the embodiment of FIGS. 1*a* and 1*b*, a punch 4 pierces a dish-shaped wall 22 of the foil-on-foil dose chamber 2. The punch 4 then passes through the chamber 2 to eventually contact a cutter 1, either directly or indirectly, that lies against a different portion of the dose chamber structure. Further movement causes the cutter 1 to move with the punch 4, away from the dose chamber 2. A portion of the barrier layer, attached to the cutter, is ruptured and moved away from the dose chamber along with the cutter. Rupture of the barrier layer provides a fluid opening between the dose chamber and an air inlet 51 and/or an air outlet 52.

It is to be appreciated that in the embodiment of FIGS. 3*a* and 3*b*, the cutter 1 does not actually move through the barrier layer to cause the rupture. Instead, the cutter pulls the barrier, causing tension and/or urging the foil into contact with another feature of the delivery device, which then causes the rupture. With this in mind, it is to be appreciated that the term “cutter” as used herein, refers to any structure that causes a barrier of a dose chamber to rupture or otherwise causes the dose chamber to open, whether through direct contact with the cutter, through stressing the barrier in a manner that causes rupture (e.g., tensioning the barrier), or through an urging of the barrier into contact with another feature that cuts or pierces the barrier to cause a rupture. It is also to be appreciated that although the cutter is shown in several embodiments herein as rupturing a barrier layer that is relatively flat, that according to other embodiments, the barrier layer that is ruptured by the cutter may be formed with different shapes.

FIG. 4 shows one embodiment of a delivery device that includes a cutter 1 positioned internally to a dose chamber. The device includes a mouthpiece 5 with an air outlet 52 through which air laden with dose 3 is delivered. The air pathway through the device includes an air inlet 25, a dose chamber air inlet channel 24 (See FIG. 7), an air bypass channel 23, and a mouthpiece air outlet 52. A flat, upper foil layer 21 and a dish-shaped, lower foil layer 22 form a foil-on-foil dose chamber 2 that is positioned within the delivery device. A disc shaped cutter 1 is incorporated internally to the dose chamber, seated in an upper portion of the dish-shaped foil layer and lying adjacent to an internal portion of the flat foil layer. A powdered dose 3 is positioned in the chamber 2 between the cutter and a lower portion of the dish-shaped lower foil, although the dose could be positioned on top of the cutter in other embodiments. An actuation button 41 that includes a punch 4 and is slidably received in a body or housing 6 of the delivery device. The device of FIG. 4 is readied for use by moving the actuation button 41 between a first position, as shown in FIG. 5, where the dose chamber 2 is sealed, and a second position, as shown in FIG. 6, where the punch has been moved to cause the cutter to rupture the barrier providing access to the dose chamber.

FIGS. 5-8 illustrate, among other features of the delivery device, the air pathway along which air may flow through the device to entrain dose for delivery to a user. FIGS. 5 and 7 are horizontal and vertical cross-sectional views, respectively, that each show the dose chamber air inlet channel 24. FIG. 6 is a vertical cross-sectional view showing the dose chamber air outlet channel 26, and FIG. 8 is a horizontal cross-sectional view showing the bypass channels 23. To use the delivery device, a user first depresses the actuation button 41 to move the punch to puncture the lower foil layer of the dose chamber. Further movement of the actuation button causes the punch to contact and move the cutter to rupture the barrier of the dose chamber, as described above. With the dose chamber now opened, a user may inhale through the mouthpiece 5 to draw air into the delivery device through the air inlet 25. A portion of the air entering the inlet 25 passes into the dose chamber 2 through a dose chamber air inlet channel 24, as is shown in FIGS. 5 and 7. In the dose chamber, the air mixes with and entrains powdered dose or other substances therein before exiting the chamber through the dose chamber air outlet channel 26 that leads to a mixing chamber 27. A portion of air that enters the inlet 25 enters a bypass channel 23, as shown in FIG. 8, and moves through the mouthpiece inlet 51 and into the mixing chamber 27 without passing through the dose chamber. Air that flows through both the bypass and the dose chamber mixes in the mixing chamber to further disperse and de-agglomerate powdered dose before exiting the device. A flow straightener 28, downstream from the mixing chamber 27, reduces turbulence in the air flow prior to delivery to a user through the air outlet 52.

Figure 9:
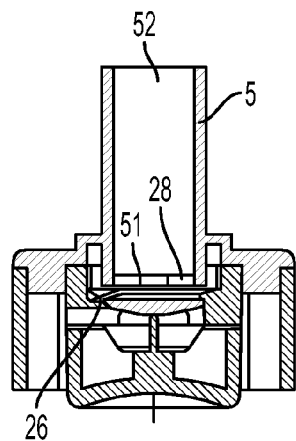
FIG. 9 shows an alternate arrangement for a flow straightener for the FIG. 4 embodiment along the cross section of FIG. 5.

Air passageways in the delivery device may be configured to accomplish different effects. By way of example, dose chamber air inlet channels 24 may be oriented to create swirling air patterns within the dose chamber, which may help to entrain powdered dose. According to some embodiments, the dose chamber air inlet(s) 24 are oriented somewhat downwardly into the dish-shaped portion of the dose chamber. Additionally or alternatively, the dose chamber air inlets 24 may be oriented to direct air circumferentially about the dose chamber, as shown in FIG. 7. The dose chamber air outlet channel and/or bypass channels may, additionally or alternatively, be configured to create further air swirling and mixing within the mixing chamber 27 of the delivery device. The bypass 23 and dose chamber air outlet channel 26 shown in FIGS. 4 and 8 are configured to direct air tangentially about the mixing chamber, creating a cyclone effect therein. This may serve to further mix and de-agglomerate any powdered dose before delivering the dose to a user. It is to be appreciated that the orientation of air passageways illustrated with respect to the embodiment of FIGS. 4-8 is but one possibly orientation, and that others are also possible and contemplated.

Passageways may be sized to control the flow rates and/or volumes through particular portions of a delivery device. By way of example, in the embodiment of FIGS. 4-8, the dose chamber air outlet 26 is smaller in cross-section than either of the bypass channels 23. This may promote a greater volume of flow through each of the bypass channels than through the dose chamber, which may help meter the flow of dose-laden air through the device, or control the rate of dose metering from the dose chamber. The relative size of dose chamber inlets 24, outlet(s) 26, and/or bypasses 23 may be modified to adjust the rate at which dose is metered, according to some embodiments.

A flow straightener 28 is positioned at the outlet of the mixing chamber 27 to reduce air swirling or turbulence as dose-laden air exits the delivery device. An air stream having reduced turbulence may flow more readily toward a user’s lungs, and be less likely to impact walls of the user’s mouth, throat, and/or esophagus, where dose may become lodged. The flow straightener shown in FIGS. 5-6 includes multiple openings, arranged in parallel to one another, through which flow that exits the mixing chamber passes. The parallel orientation and smaller cross-section of the openings urges flow toward a laminar state, reducing turbulence. It is to be appreciated that other types of flow straighteners may also be used, such as straighteners that include different shapes or lengths of openings, or flow straighteners positioned at different locations within a delivery device. By way of example, a flow straightener 28 may be positioned closer to a dose chamber outlet channel 26 and at the mouthpiece inlet 51, as shown in the embodiment of FIG. 9. The embodiment also includes a longer air outlet 52 to provide increased distance for the reduction of air turbulence prior to delivery to a user. Other embodiments may lack a flow straightener altogether, as is to be appreciated.

The cutter 1 (which may be a disc element) may help hold the dose in a particular area of the dose chamber. By way of example, in the embodiment of FIGS. 4-8, the cutter positions most if not all of the dose near the lower portion of the dish-shaped layer. In the embodiments of FIGS. 1a-1b, the dose is held in a substantially toroidal portion of the dose chamber that is formed in part by the cutter, both before and after the dose chamber has been opened. The embodiment of FIGS. 2a and 2b similarly holds the dose in a substantially toroidal shape that changes form as the lower, dish-shaped foil layer is deformed to open the dose chamber. Configuring a delivery device/dose chamber such that all or most of a dose is located in a consistent place from device to device (or from dose chamber to dose chamber in multi-dose devices) may promote more consistent dose delivery characteristics.

Figure 10A:
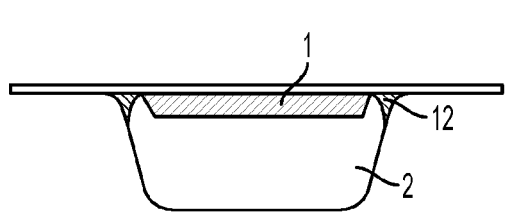
FIGS. 10a and 10b show schematic views of a dose chamber in which a ring or other element is arranged around the cutter.
Figure 10B:
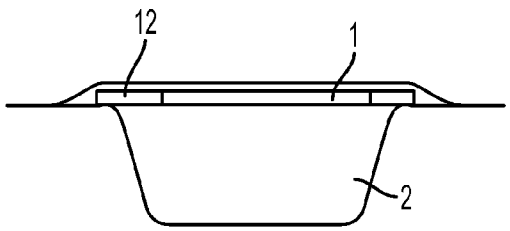
Figure 10C:
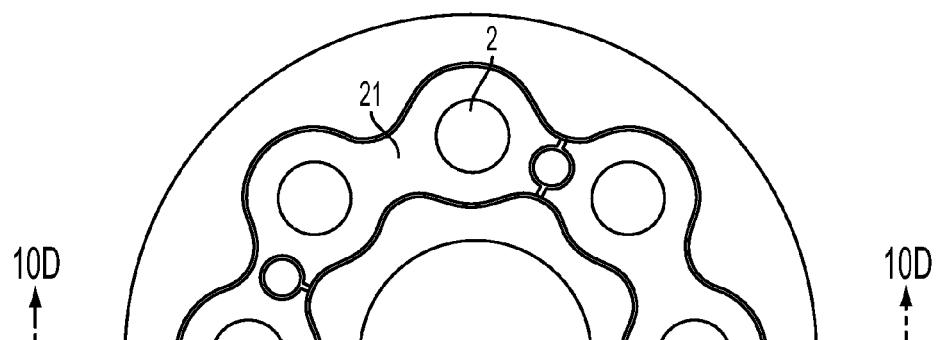
FIG. 10c shows an illustrative embodiment in which multiple dose chambers are arranged in a circular array.
Figure 10D:
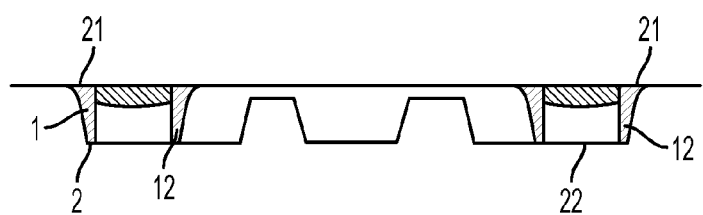
FIG. 10d is a cross-sectional view along the line 10d-10d in FIG. 10c.

Contact between the cutter and a wall of the dose chamber, other than the wall that is to be ruptured, may prevent dose from becoming lodged at a seam where the rupturable barrier mates with other walls of the dose chamber. For instance, in the embodiment of FIGS. 1a-1b, contact between the cutter and the dish-shaped lower layer prevents dose from entering the joining region between the flat layer and the dish-shaped layer. According to another embodiment, as shown in FIGS. 10a and 10b, a ring of relatively rigid material 12 (e.g., in the form of a ring in this embodiment) may be positioned about the cutter 1 to prevent exposure of dose 3 to a joining region between layers of the foil-on-foil seal. The overhang of the ring 12 may also promote recirculation of air within the dose chamber, which may help break up dose prior to being delivered from the dose chamber. The ring 12 may be formed integral with the cutter, including a frangible joint that is broken when the cutter 1 is moved, or may be separate altogether from the cutter 1, as aspects of the invention are not limited in this respect. Additionally, although referred to as a ring 12, it is to be appreciated that other shapes may be positioned between the rupturable barrier and lower structure of a dose chamber to prevent dose from becoming lodged or trapped at a joining region. It should be appreciated that dose chambers 2 may be provided in any suitable array arrangements, such as that shown in FIG. 10c in which dose chambers are arranged in a circular array. The chambers 2 are arranged in a way similar to that in FIG. 10a in which a ring 12 is provided for each dose chamber 2 and surrounds a cutter 1.

Movement of a cutter 1 from the closed position to the open position may be guided by different features of a delivery device. In the embodiment of FIGS. 1a/1b and 3a/3b, a receptacle in the cutter is received by a corresponding structure in the delivery device mouthpiece or body to guide the cutter linearly toward the open position. In the embodiment of FIGS. 2a/2b, the interaction between the peripheral edges of the cutter 1 and the internal walls of the delivery device body helps to guide the cutter to the open position. Similarly, internal walls of the embodiment shown in FIGS. 4-9 guide the cutter in movement toward the open position. Other configurations are also possible, as those shown and described with respect to the embodiments of FIGS. 1a/1b, 2a/2b, 3a/3b, and 4-9 are merely exemplary.

According to some embodiments, a positive stop may be contacted by the cutter when in the open position, to prevent further movement. Each of the embodiments of 1a/1b, 2a/2b, 3a/3b, and 4-9 include some form of positive stop to prevent movement of the cutter beyond the open position. In the embodiments of FIGS. 1a/1b, 2a/2b, and 3a/3b, interaction between the receptacle and corresponding post-like structure prevents further cutter movement. In the embodiment of FIGS. 4-9, a ring shaped seat receives the cutter, when in the open position, to prevent further movement. The positive stop in the embodiment of FIGS. 4-9 may also help straighten the cutter if the cutter becomes cocked during movement. By way of example, a leading edge of the cutter that has become cocked in movement may contact the positive stop first, and prevent further movement of the leading edge, allowing the cutter to straighten or become uncocked as the trailing edge moves into contact with the positive stop.

Figure 11A:
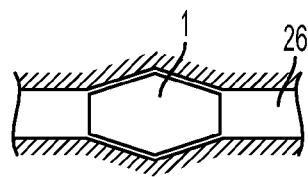
FIGS. 11a-11c show alternate shapes for a cutter in the form of a disc element.
Figure 11B:
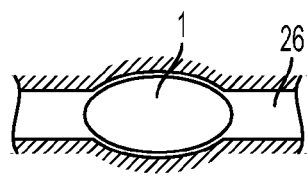
Figure 11C:
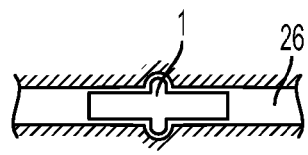

In other embodiments the cutter and/or adjacent walls of the delivery device may be shaped to prevent cocking or lateral movement as the dose chamber is opened and/or to retain the cutter in position after the dose chamber is opened. FIG. 11a shows one embodiment where the cutter, in this embodiment in the form of a disc element, includes a diamond cross-sectional shape that conforms to similar geometry in the body of a delivery device. Thus, a disc element is not restricted to a circular, puck-like shape, but may include other shapes. The edges of the diamond shape prevent the cutter from moving undesirably, e.g., upstream or downstream along the dose chamber air inlet passageway 24 or outlet passageway 26, where the cutter might otherwise impede the flow of air through the device when in the open position. FIG. 11c shows yet another embodiment where the cutter includes ribs that ride along grooves in the delivery device body as the cutter is moved toward the open position. FIG. 11b shows an oval shaped cutter and delivery device body that guides the cutter toward a positive stop at the open position. It is to be appreciated that the shapes and structures discussed with respect to FIGS. 11a-11c are merely but three examples of features that might prevent misalignment and/or cocking of a cutter and/or prevent cutter movement after opening, and that other features are additionally contemplated.

Delivery devices may include features that retain a cutter in the open position for dose delivery and/or after a dose has been delivered. For instance, in the embodiment of FIG. 11c, the cutter may become lodged in the end of a tapered delivery device body. The cutter may be retained in this position, even after a punch 4 has been retracted. This may prove helpful in embodiments where dose delivery occurs after the punch has been retracted and/or in embodiments that include multiple dose chambers, as discussed in greater detail herein.

Figure 12:
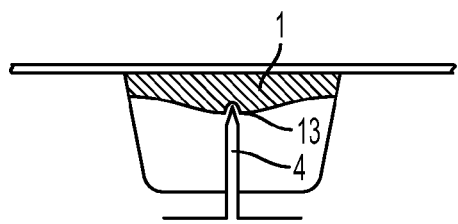
FIG. 12 shows an embodiment in which a cutter includes a recess to receive a portion of a punch.

The interface between the cutter and punch, or other feature that moves the cutter, such as a puller, may promote controlled movement of the cutter from the closed to the open position. As shown in FIG. 12, the cutter may include a notch or recess 13 that receives a portion of the punch 4. The recess 13 may help the punch contact the cutter at a central position that helps the cutter to move evenly, in a controlled manner from the closed to open position. As illustrated, the recess is located at a center position of the cutter, although other positions are also possible. The interaction between the punch and the cutter may, additionally or alternatively, result in a tip of the punch being embedded into the cutter to help fix the position of the punch relative to the cutter.

Control over movement of the cutter may, additionally or alternatively, be aided by the interface between the cutter and a wall of the dose chamber that is deformed or punctured to move the cutter. In FIGS. 2a and 2b, the cutter includes a post that is either formed integrally with or fastened to the dish-shaped dose chamber wall. In this respect, the post will not move relative to the dish shaped chamber wall, when the wall is deformed to move the cutter. In some embodiments, the wall that contacts the post (or other feature) of the cutter may include a receptacle that prevents the post from sliding relative to the wall during cutter movement. Other features are also possible and are contemplated, although not explicitly described herein.

Figure 13:
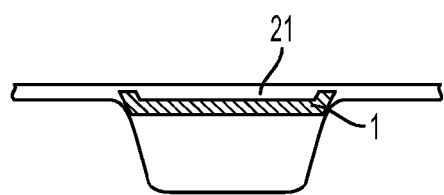
FIG. 13 shows an embodiment in which a cutter includes a raised edge or edges at a periphery to help concentrate a cutting force.

Embodiments of the cutter may include features that promote rupture of the barrier material. By way of example, FIG. 13 shows a cutter 1 that includes raised edges that contact and promote rupture of the barrier material 21. This occurs by reducing the contact area between the cutter and barrier material, such that greater pressure exist therebetween for a given force applied by the cutter. Creating a recess, in this manner, may compensate for any bending that might otherwise occur as the cutter is moved against the barrier material, which might otherwise reduce the pressure at peripheral edges of the cutter. According to other embodiments (not shown), the cutter may include raised points, edges, or other stress inducing features that promote rupture of the barrier material as the cutter is moved thereagainst. Additionally or alternatively, cutters may flex when moved to concentrate forces at particular interaction areas with a barrier to be ruptured.

The cutter, when in the open position and in the form of a disc element, may help direct air in a particular manner. FIGS. 2a, 2b, 3a, and 3b show, for instance, one type of configuration where the cutter, when in the open position, provides both structure to divert air into the dose chamber and a portion of a bypass for air to pass through a delivery device without entering the dose chamber. FIGS. 1a and 1b show a cutter that includes additional structure to direct flow in a more downward direction, as the flow passes through the dose chamber, which may result in increased mixing and dose dispersion. According to other embodiments, such as that shown in FIGS. 4-9, the cutter may largely move out of the way of flow through a dose chamber, when in the open position.

The dose chamber, when opened by the cutter, may include different shapes, sizes, and configurations of air inlets and/or air outlets. By way of example, in FIGS. 1a/1b, the dose chamber, when opened, is in fluid communication with separate air inlet channels and air outlet channels. According to other embodiments, a common air pathway to the dose chamber may provide a channel both for air to enter and exit the dose chamber.

The punch is shown as a pointed structure in the various embodiments illustrated herein. It is to be appreciated, however, that the punch may alternatively be formed of other shapes. By way of non-limiting example, the punch may be formed from sheet metal, and have flat blade-like shape, according to some embodiments. According to other embodiments, the punch may include a cross-shaped cross-section, or other shapes. Embodiments of the punch may be made of various materials, including but not limited to, metals and plastics. The punch may be integrally formed with the actuation button or other structure that holds the punch, or may be manufactured separately and fastened thereto, as aspects of the invention are not limited in this respect.

A barrier may be formed of various materials. According to some embodiments, the barrier includes an aluminum foil that is substantially impervious to light and moisture, although in other embodiments, barriers may be permeable to some degree of moisture and light. The barrier may be readily adhered to other barriers, such as for foil-on-foil embodiments described herein, or to other structures of a delivery device, that are often formed of plastic. Adhesives, heat weld, friction welds, and other fastening techniques may be used to affix barriers and to provide a seal between the barrier and mating structure. Air may also flow through a hole in the punch itself, as shown for example, in the embodiment of FIG. 18, or through holes created by a punch, according to some embodiments.

FIGS. 14a-14f show another embodiment of a device that may be used to deliver a dose to a subject. As can be seen in the upper and lower perspective views of FIGS. 14a and 14c, and the exploded view of FIG. 14b, the illustrated device includes an upper housing 61, a central housing 62, and a lower housing 63. A dose capsule, including a dose chamber 2, is positioned in a cavity that lies between the lower housing 63 and the central housing 62. A punch 4 is operably connected to the lower housing 63 and may be depressed by a user to urge a cutter 1 to rupture an upper barrier of the capsule to ready the device to deliver a dose to a subject in any of the various ways described herein. A toroidal shaped mixing chamber 27 is positioned to receive dose laden air from the dose chamber for further metering and mixing. Additionally, a classifier 29 receives air from the mixing chamber 27 prior to delivery of the dose to a subject through the inlet 51 of the mouthpiece 5.

Figure 14B:
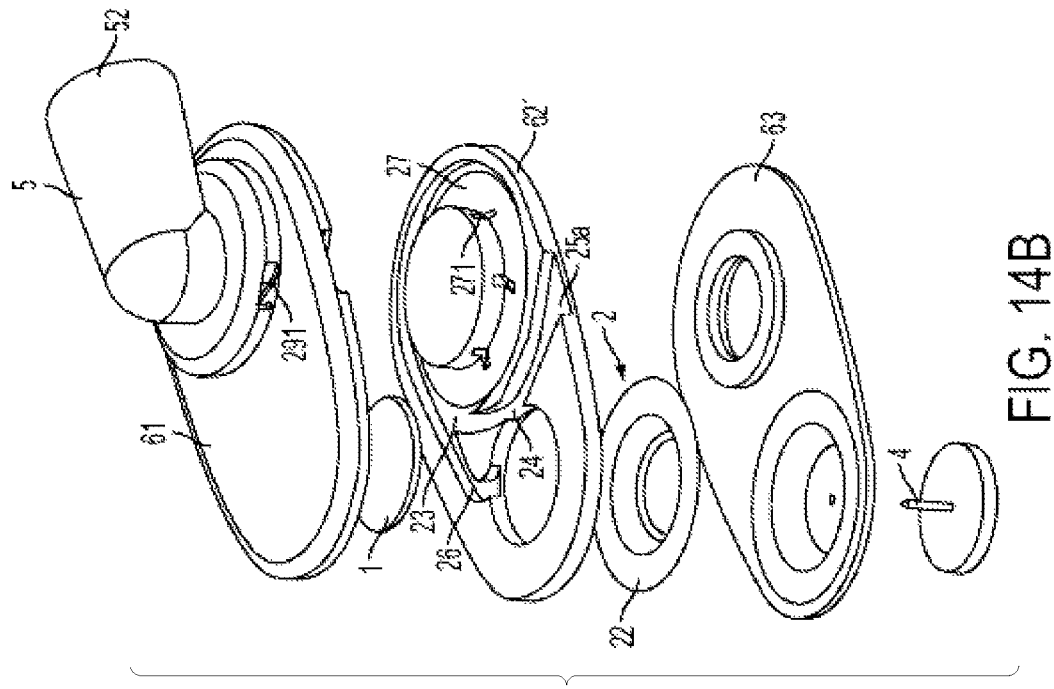
FIG. 14b shows an exploded view of the FIG. 14a embodiment.
Figure 14A:
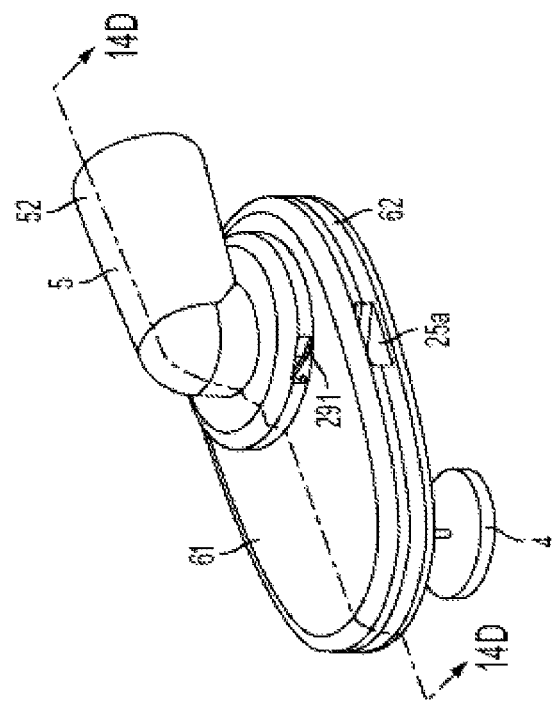
FIG. 14a shows a top front right perspective view of another embodiment of a dose delivery device.
Figure 14C:
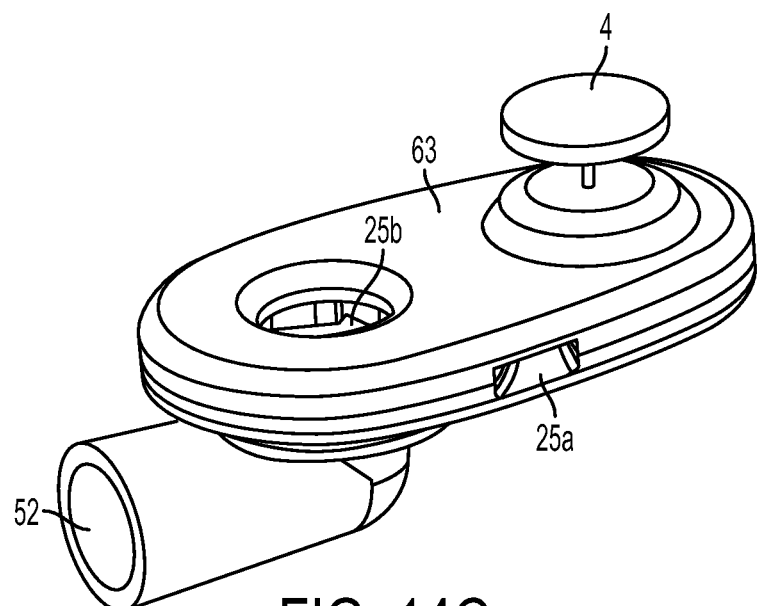
FIG. 14c shows a bottom rear left perspective view of the FIG. 14a embodiment.
Figure 14D:
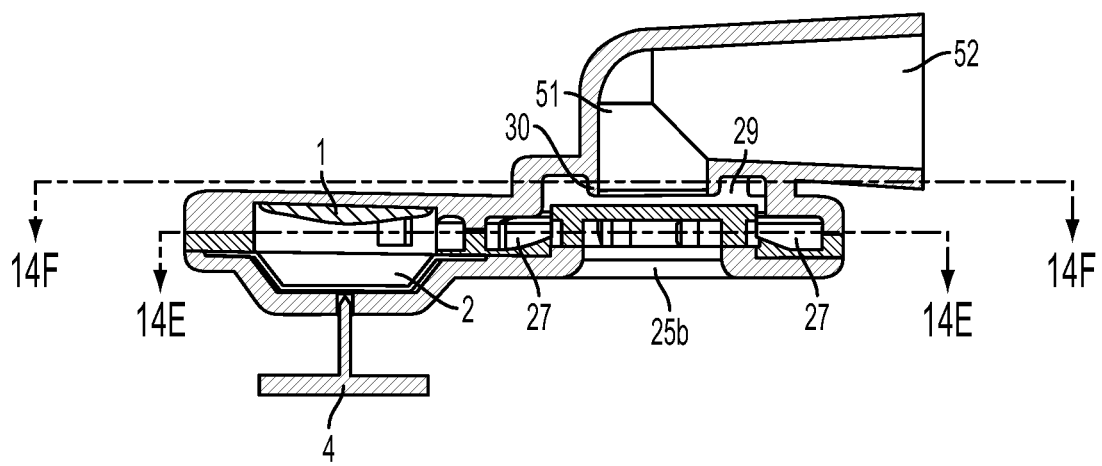
Figure 14E:
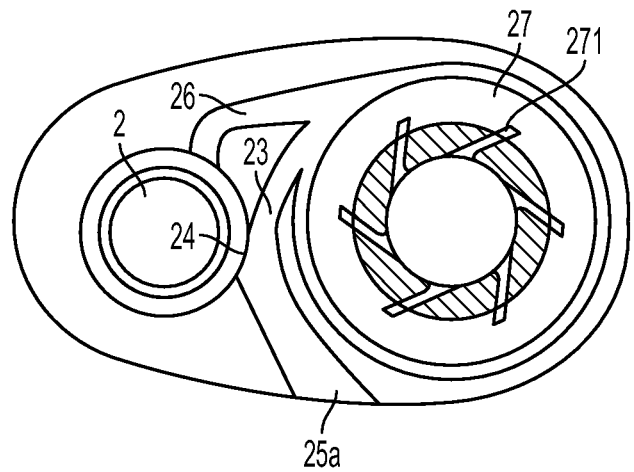
FIG. 14e shows a cross sectional view of the FIG. 14a embodiment along the lines 14e-14e in FIG. 14d.
Figure 14F:
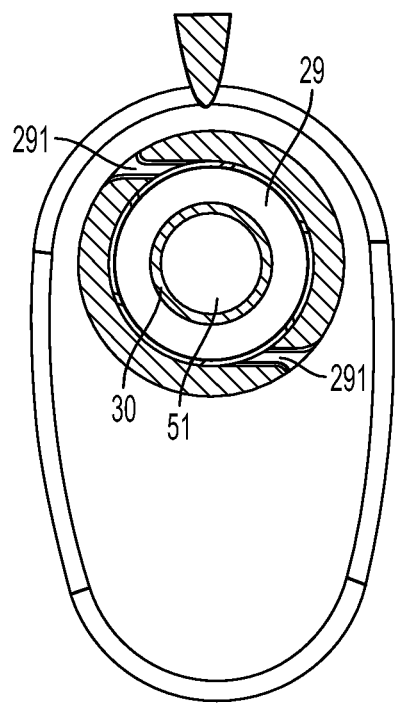
FIG. 14f shows a cross sectional view of the FIG. 14a embodiment along the lines 14f-14f in FIG. 14d.
Figure 15A:
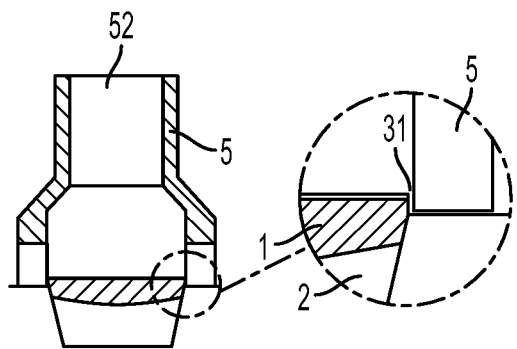
FIGS. 15a-15c show illustrative embodiments in which the dose chamber and/or cutter include features to help align the cutter with a receiving structure.
Figure 15B:
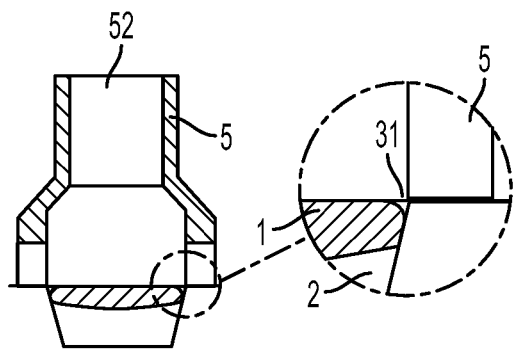
Figure 15C:
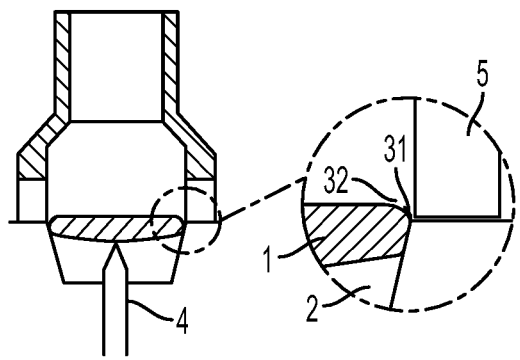
Figure 16:
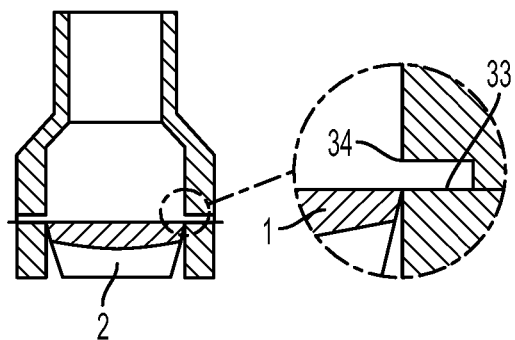
FIG. 16 shows an illustrative embodiment in which the receiving structure of a dose delivery device includes a recess and cutting edge.
Figure 17:
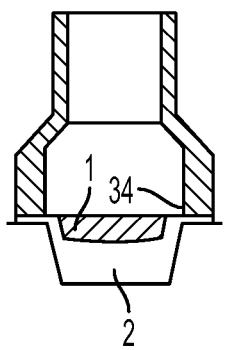
FIG. 17 shows an illustrative embodiment in which the cutter is sized to operate with a receiving structure of a dose delivery device.

FIGS. 14c-14e show the internal air flow pathways of the embodiment illustrated in FIGS. 14a and 14b, as taken along the cross-sections shown in FIGS. 14a and 14c. An air inlet 25a is positioned on the side of the device to receive air, at least part of which is to pass through the dose chamber of the capsule to entrain dose for delivery. A mixing chamber air inlet 25b is positioned on the underside of the device, beneath the mixing chamber 27, to receive a primary flow of air into the mixing chamber 27 from the external environment to promote mixing. Additional classifier air inlets 291 are positioned on the upper housing and are configured to direct air from the external environment to promote swirling/mixing in the classifier 29.

In use, with the dose chamber readied to deliver dose, a user inhales through the device outlet to pull air through the device. Air that enters through the air inlet 25a moves towards a scoop-like diverter structure that directs a portion of the air into the dose chamber air inlet channel 24 to the dose chamber 2 while the remaining air moves downstream along a bypass 23 and toward the mixing chamber 27. Air that enters the dose chamber 2 entrains dose and then passes back through the dose chamber air inlet 24 and/or through the dose chamber outlet 26 that leads, as shown in FIG. 14e, to the mixing chamber 27. A portion of the air in the dose chamber may be recirculated and directed back through the dose chamber for later flow through the air inlet 24 or outlet 26.

The flow of air through the dose chamber causes dose therein to be pushed outwardly against the interior wall of the dose chamber and may spread the dose evenly about the interior wall. Air then flows across the surface of the dose, entraining particles of the dose as the flow progresses about the dose chamber. Entrained particles may tumble about the chamber and be broken down in to smaller particles for improved delivery. Additionally, larger particles entrained within the flow may have too much momentum to turn toward the dose chamber outlet 26, and may continue on a path toward the entryway wall of the dose chamber near the dose chamber inlet 24 and become entrained in the flow of air that is entering the chamber through the inlet 24. In this respect, the larger particles may be recirculated back through the chamber to be de-agglomerated into smaller particles or may remain indefinitely within the chamber.

Air enters the mixing chamber 27 from multiple inlets 271 to create swirling patterns that further mix dose within air that is delivered to a subject. As described above, air laden with dose enters the mixing chamber 27 both from the bypass 23 and the dose chamber outlet 26, through a primary inlet. The primary inlet, positioned on at outer portion of toroidal mixing chamber, is configured to direct air substantially tangentially about the toroidal mixing chamber, as may be viewed in FIG. 18. Air also enters the toroidal mixing chamber from inner positions of the torus through the air inlets 271 on the underside of the mixing chamber 271. Angled fins are positioned to also direct air that enters the mixing chamber 27 from the central area of the torus 27, tangentially about the mixing chamber 27 in the same direction as air received through the primary air inlet. It is to be appreciated, however, that other embodiments may have air entering the mixing chamber in different directions.

Air laden with dose exits the mixing chamber 27 through a mixing chamber outlet positioned at the inner portion of the torus, as shown in FIG. 14d. As air moves around the torus-shaped chamber, centrifugal force urge the dose outward, against the outer walls of the chamber. This motion may cause the dose to spread out over the outer walls. Air passing over the dose may then act to peel dose away from the outer walls, such that dose may be metered from the mixing chamber in a manner similar to how dose is metered from the dose chamber, as described above and as described in U.S. patent application Ser. No. 12/168,445, which is hereby incorporated by reference in its entirety. Larger agglomerated particles, which have greater mass, may tumble about mixing chamber and break into smaller particles before exiting at the inner portion of the chamber.

Dose laden air enters a classifier 29 after exiting the mixing chamber 27, as may be seen in FIGS. 14*d* and 14*f*. Additionally, air enters the classifier 29 from the external environment through a pair of classifier air inlets 291, as shown in FIG. 14*f*. The classifier air inlets 291 direct air substantially tangentially into the classifier 29 to induce a swirl pattern that rotates in the same direction as that of the mixing chamber 27, although different configurations are possible and are also contemplated. Dose typically swirls about the classifier momentarily before moving underneath the annular lip shaped obstacle 30 at the entrance to the outlet passageway. The lip 30 may additionally help retain larger particles within the device until they are broken down for delivery to a subject.

The applicants have appreciated that having multiple dose metering features arranged serially within a device, may provide for improved dose delivery. That is, in the embodiment of FIGS. 14*a*-14*f*, dose is initially metered from the dose chamber of the capsule. This results in a flow of dose laden air that travels toward the mixing chamber 27 in a stream that is then further dispersed and metered in the mixing chamber. Serially arranged features that meter dose, like those of the embodiment shown in FIGS. 14*a*-14*f*, may prove particularly beneficial for the delivery of neat drugs, among other types of doses.

Single dose delivery devices may be configured for one time use, or may be configured for multiple uses. By way of example, the dose chamber 2 is seated in the device between middle and lower housings 62, 63 that are placed together permanently to insure that the delivery device is only used a single time. According to other embodiments, the device may be opened so that the capsule may be removed and replaced, either by a user or a manufacturer, to allow the device to be re-used. It is to be appreciated that these are but two examples of ways in which a device may be configured, and that others are possible and are also contemplated. By way of example, some embodiments may not include a separate capsule, but instead have a dose chamber that is incorporated into the housing(s) of the delivery device itself.

The dose chamber in the embodiment of FIGS. 14*a*-14*f* is configured to prevent movement of dose from the chamber prior to intended delivery. That is, the opening to the dose chamber and the dose chamber outlet 26 are positioned such that, when the device is held by a user, any dose will likely be positioned against the wall of the dose chamber that is opposite to the dose chamber inlet and outlet 24, 26. Typically, a user will hold the device with the outlet 52 oriented upward and the dose chamber side of the device at a lower position to depress the punch 4. The device will then typically be moved to a horizontal position for dose delivery. In neither of these positions, or any in between will gravity draw dose from the chamber 2, thereby promoting retention therein until delivery.

According to some embodiments, features may be included in the delivery device and/or the capsule to promote proper alignment and seating of the capsule. As may be appreciated, misalignment of a capsule that includes a cutter may prevent the cutter from being properly moved to an open position, which may adversely affect the function of a device or render a device inoperable. According to some embodiments, a capsule may include a raised lip that is received by a feature of the device to ensure alignment. In the embodiment of FIG. 15*a*, a cutter internal to the dose chamber 2 forms a lip 31 in the upper foil layer. In the embodiment of FIG. 15*b*, the cutter 1 includes a relieved, chamfered or tapered edge 32 that helps the cutter 1 self align with a receiving opening in the mouthpiece 5 (or other receiver). In the embodiment of FIG. 15*c*, the cutter 1 includes a tapered edge 32 and the chamber 2 includes a lip 31 or shoulder that helps the cutter 1 to be properly received by the mouthpiece 5. It should be appreciated that other features may additionally or alternatively be used to align a capsule with respect to a delivery device.

Delivery devices and/or capsules may include features that promote consistent rupture of barrier materials from device to device. As is to be appreciated, a feature of the delivery device that causes an internal cutter of a dose chamber to rupture a barrier material, whether in cooperation with a dose chamber cutter or alone, may be spaced apart from the barrier material when in the chamber is closed. Manufacturing variation, among other issues, may cause this spacing to vary from device to device such that cutters internal to a dose chamber may have to travel different distances to cause a barrier to rupture. With this in mind, the applicants appreciate that features that allow a punch, and thus cutter to be moved with a relatively even force may allow a barrier to be ruptured with a similar applied force, even for cutters that have to move different distances.

FIG. 16 shows one embodiment of a delivery device and dose chamber configured to provide a relatively even force over a range of distances that a cutter may travel. As shown, the foil on foil interface of the dose chamber 2 is captured between the housings of the delivery device at a position that is spaced away from the cutter/barrier interface. The foil on foil portion may bend upward as the cutter 1 is moved upward, thereby reducing the amount of force required as compared to a capsule that is captured at a position closer to the foil on foil interface. The mouthpiece 5 or other body may include a recess 33 that permits upward movement of the cutter 1 with little resistance, and an interface 34 (such as a cutting edge) that engages the foil barrier layer and cutter 1 to pierce the chamber 2. Additionally or alternatively, a cutter internal to a dose chamber may be spaced from the foil on foil interface 34 to provide additional material for flexing/movement, as shown in FIG. 17. According to other embodiments, the housing of the delivery device itself may flex to allow cutting features to move toward the barrier. By way of example, the upper housing shown in FIGS. 14*a*-14*f*, which is typically compressed as a user depresses the punch, may flex to allow a cutting feature of the device to move toward a barrier to be ruptured.

Figure 18:
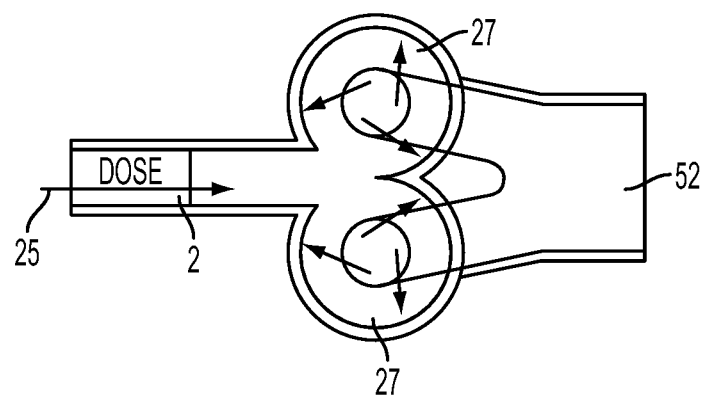
FIG. 18 shows an illustrative embodiment of a dose delivery device including dual torus shaped dose metering chambers.

According to some embodiments, delivery devices may include dose metering chambers arranged in parallel. FIG. 18 shows one such embodiment that includes dose chambers 2 that each receive air from a common air inlet 25, and that provide dose laden air to a common outlet 52. In the illustrated embodiment, a single dose begins in the common air inlet channel. Air, drawn through the device, pulls portions of the dose into each of the pair of torus shaped dose metering chambers 27 through inlets positioned on the outer portion of each torus. Air and dose then swirl about each of the metering chambers 27 to disperse and meter dose, as described herein with respect to dose metering chambers of other embodiments.

FIGS. 19*a* and 19*b* shows another embodiment, like that of FIG. 18, but with dose metering chambers 27 that comprise cyclone type chambers. Air and dose that enter the cyclone chambers 27 are directed in a downward swirling pattern toward the bottom of each of the chambers. From the bottom of the chamber, air laden with dose may move upward and enter an air outlet channel that is centrally located in each chamber. As shown, the cyclone chambers 27 may taper at points closer toward the bottom, although other embodiments may include different configurations. The side view of FIG. 19*b* also illustrates a dose chamber in which dose may be held prior to delivery. The dose chamber includes an internally positioned cutter 1, as described herein with respect to other embodiments, but may alternatively include other configurations of dose chambers.

FIGS. 19*c* and 19*d* show a schematic representation of one embodiment of delivery device with features similar to that of FIGS. 14*a*-14*f*, but configured to simultaneously deliver doses from two different dose chambers. The capsule, as shown, includes two separate dose chambers 1, each with a cutter 1 positioned internally. The device also includes a torus shaped mixing chamber 27 positioned downstream of each dose chamber and/or a classifier positioned downstream of each torus shaped chamber. Such embodiments may prove particularly useful in combination therapy applications, where it may be desirable to administer multiple doses at the same time, but to prevent mixing of the doses until delivery.

It is to be appreciated that although various embodiments of the delivery devices are discussed and illustrated herein as a single dose device, that a plurality of any of the dose chambers may be incorporated into a device that may deliver multiple doses. Incorporating multiple dose chambers into a common device may allow some features of a delivery device to be shared among different dose chambers. By way of example, a multi-dose device may include a common outlet that is used to deliver, sequentially, doses from each of the dose chambers to a subject, when needed. Other features may be shared among the different dose chambers of a common, multi-dose device, such as a single actuation button and/or punch that is moved sequentially into registration with each dose chamber to move an opening mechanism between a first and second position to ready a dose for delivery, or a cassette is moved into registration with the punch. Additionally or alternatively, a multi-dose configuration may reduce the overall cost per dose to be delivered from a delivery device.

FIGS. 20*a*-20*d* illustrate one embodiment of a multi-dose device. FIGS. 20*a* and 20*b* show exploded assembly views of the device, taken from an upper and lower view, respectively. FIGS. 20*c* and 20*d* show cross-sections of the multi-dose device, both with a dose chamber in an closed position and an open position, respectively.

The multi-dose device includes a cassette that, as illustrated, houses sixty dose chambers. The cassette includes an upper, middle, and lower housings 61, 62, 63 that are enclosed within upper and lower enclosures 64, 65. An air pathway is defined between formed structures of the upper, middle, and lower housings, although in other embodiments, the air pathway may simply include a passageway that lies over a dose chamber. Cavities in the lower housing are sandwiched between layers of barrier material (not shown in FIGS. 20*a* and 20*b*) to define the dose chambers 2. A cutter 1 having a substantially rectangular cross-section, as viewed from above, is positioned internally to each dose chamber, although the cutter could alternatively be positioned externally. The cutters lie adjacent to upper barrier material that is between the lower and middle housings 62, 63. In operation, the housings 61-63 are rotated relative to the housing to sequentially bring an outlet of the air pathway associated with each dose chamber into registration with a mouthpiece 5 of the multi-dose device, and to bring each dose chamber into registration with the punch 4. Rotation of the housings 61-63 occurs when the actuation button 41 is moved relative to the enclosures 64, 65 of the delivery device. With the air pathway and mouthpiece 5 in registration, the dose chamber 2 is opened by moving the housings 61-63 relative to a punch 4. The punch 4 pierces lower barrier material on the bottom of the lower housing 63, and then passes into the dose chamber where the punch 1 contacts the cutter 1. Further movement of the housings 61-63 relative to the punch 4 causes the cutter 1 to rupture upper barrier material on the top of the upper housing 61 by urging the cutter upward, and causing the upper barrier material to be urged upward against edges of the middle housing 62 about the dose chamber that help the cutter 1 shear the barrier material. Shearing the upper barrier material results in an opening of the dose chamber to the air pathway that lies between the upper and middle housings 61, 62 to ready a dose for delivery. It is to be appreciated that multi-dose devices may be configured differently than that shown in FIGS. 20*a*-20*d*. By way of non-limiting example, some embodiments may lack an actuation button 41 like that shown, and instead rely on movement of a mouthpiece or other component to cause the housings 61-63 to index. Other embodiments may include a plurality of punches, instead of a single punch that is sequentially used to open different dose chambers. In yet other embodiments, the punch or plurality of punches may be replaced by a puller or plurality of pullers (e.g., one puller for each dose chamber) that are arranged to engage with a corresponding cutter 1 and pull the cutter away from the dose chamber. For example, the upper housing 61 may include one or more pullers that move downwardly to engage with a cutter 1 and then move upwardly from the dose chamber 2 to pull the cutter 1 and open the dose chamber. Movement of the puller(s) may be caused by an activation button 41 and spring 67, or other arrangement. For example, upward movement of the cassette (to a position like that shown in FIG. 20*c*) may cause a puller to move relative to a cutter 1 and engage the puller and cutter 1 with each other. Subsequent movement downward (to a position like that in FIG. 20*d*) may cause the puller and engaged cutter to withdraw from the dose chamber 2 as the dose chamber 2 moves downward.

Each of the upper, middle, and lower housings 61-63 of the cassette may be made of a rigid material, at least as compared to material used to form foil-on-foil chambers described herein with respect to other illustrated embodiments. According to one embodiment, the lower, middle, and upper housings 61-63 are made of injection molded plastic, which may allow for greater dimensional control over features of the cassette and dose chambers. Any increased costs associated with forming dose chambers in such a manner may be offset by the increased number of dose chambers that may be incorporated into a single device. Additionally or alternatively, dose chambers formed in the manner of FIGS. 20a-20d may be packaged into a smaller space, which may prove advantageous for embodiments that include multiple dose chambers. It is to be appreciated that although dose chambers are described herein with respect to a multi-dose device, single dose devices may also be formed in this manner. It is also to be appreciated that features discussed herein with respect to single dose devices may additionally be applicable to multi-dose devices.

Figure 21:
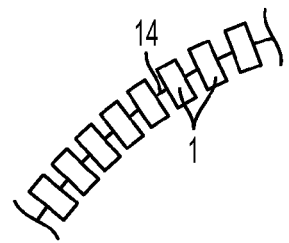
FIG. 21 shows an illustrative embodiment in which the cutter elements in the FIG. 20a embodiment are formed with a web attaching the elements together.

Cutters for a multi-dose device may be manufactured together in a manner that promotes easier assembly of the cutters into corresponding dose chambers. By way of example, FIG. 21 shows a portion of 60 cutters formed to include a common web 14. The web 14 is shaped and sized to position each of the cutters 1 in dose chambers of a cassette, which may simplify assembly. According to some embodiments, the web 14 may be separated from each of the cutters prior to barriers being assembled thereto. According to other embodiments, the web 14 may be sealed against the foil layer or the housing as a part of the cassette assembly, as aspects of the invention are not limited in this respect.

The upper and lower enclosure halves 64, 65, and cover 66 of the delivery device may at least partially enclose the cassette and may include a mechanism that brings each dose chamber of the cassette sequentially into position to ready a dose for delivery. The cover 66, when in the closed position, may additionally provide protection for the mouthpiece by preventing contaminants from entering the outlet of the device.

Figure 19A:
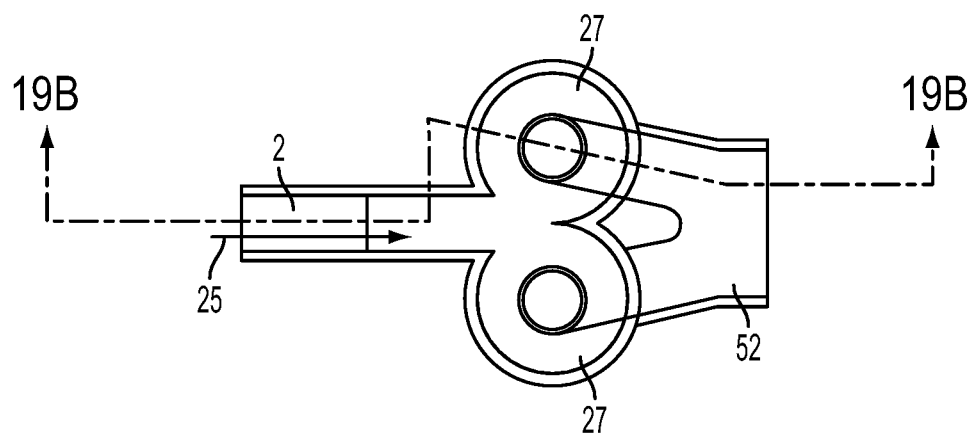
FIG. 19a shows an illustrative embodiment of a dose delivery device including dual cyclone metering chambers.
Figure 19B:
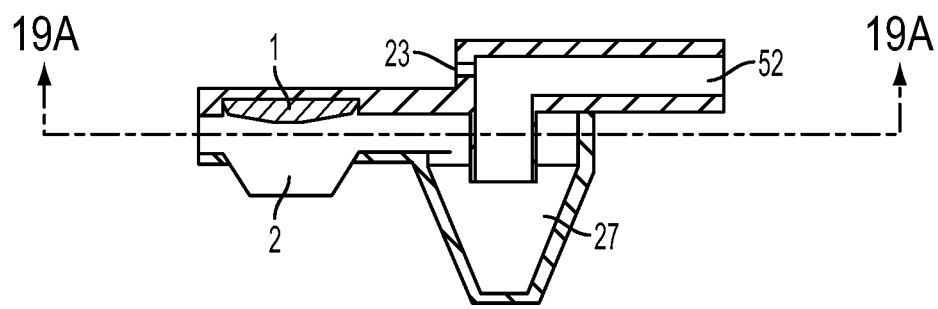
FIG. 19b shows a view of the FIG. 19a embodiment along the line 19b-19b.
Figure 19C:
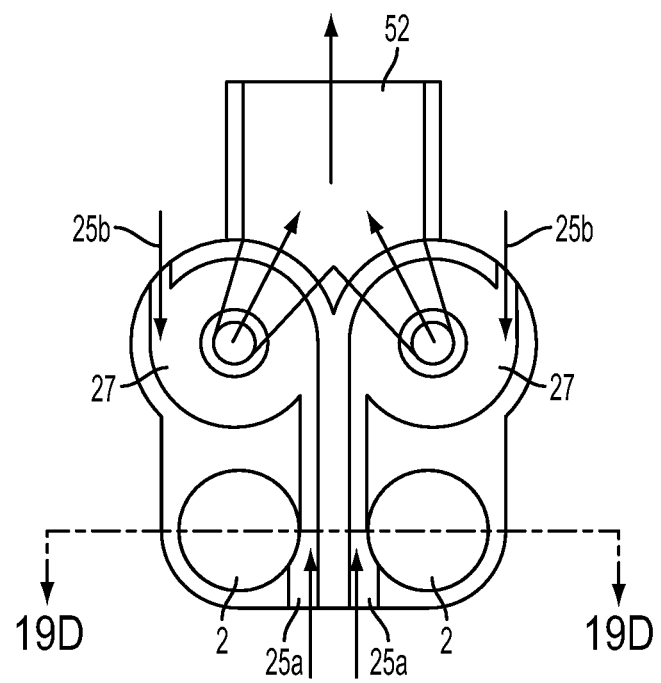
FIG. 19c shows a schematic representation of an embodiment of a delivery device similar to that of FIGS. 14a-14f, but configured to simultaneously deliver doses from two dose chambers.
Figure 19D:
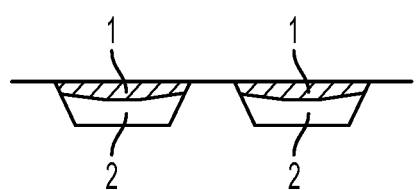
FIG. 19d shows a view of the FIG. 19c embodiment along the line 19d-19d.

A lock may be incorporated into a delivery device to prevent unwanted actuation. By way of example, the cover 66 in the embodiment of FIGS. 20a-20d may also lock the actuation button 41 in position. Lock levers attached to the lower housing, as shown in FIG. 19a, include locking protrusions that may engage either an upper or lower groove of the actuation button 41 to hold the button in either a lower or upper position, respectively. Rotation of the cover 66 from the closed position to the open position causes cam surfaces on the cover 66 to rotate and contact corresponding cam surfaces on the lock levers. Interaction between these cam surfaces causes the lock levers to splay outwardly, disengaging the locking protrusions from the grooves on the actuation button to allow the button to move. Rotating the cover 66 back to the closed position allows the lock levers and locking protrusions to move back into grooves on the actuation button to lock the button in place. It is to be appreciated that the lock discussed with respect to FIGS. 20a-20d is but one type of lock that may be incorporated into a delivery device, and that variations of this lock are also contemplated as well as delivery devices that lack locks altogether.

Figure 20A:
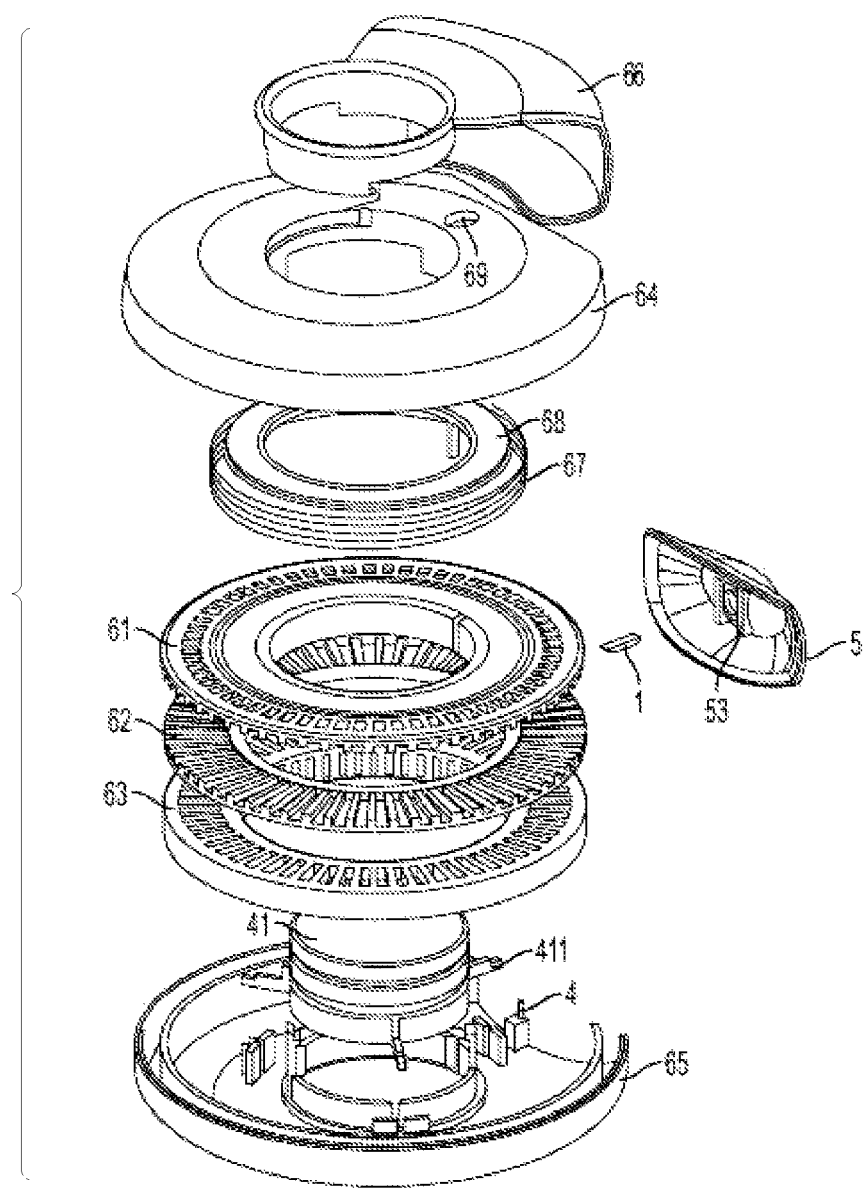
FIG. 20a shows a top exploded view of an illustrative embodiment of a multi-dose chamber delivery device.
Figure 20B:
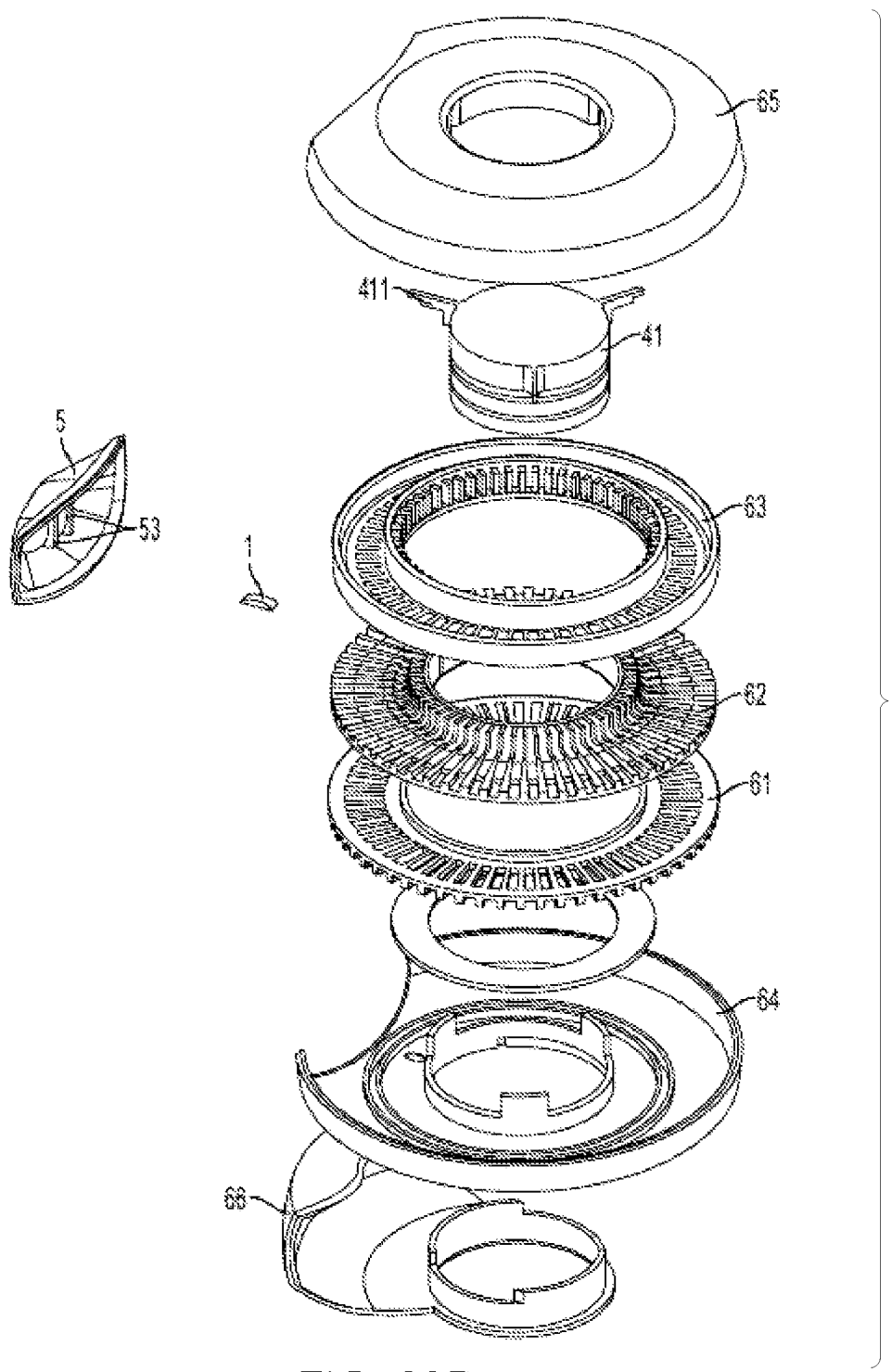
FIG. 20b shows a bottom exploded view of the FIG. 20a embodiment.
Figure 20C:
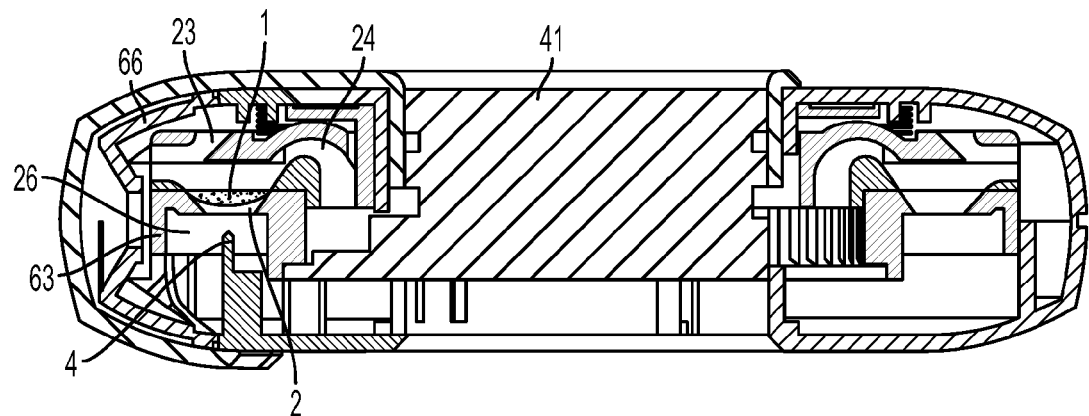
FIG. 20c shows a cross sectional view of the FIG. 20a embodiment with a dose chamber positioned above a punch.
Figure 20D:
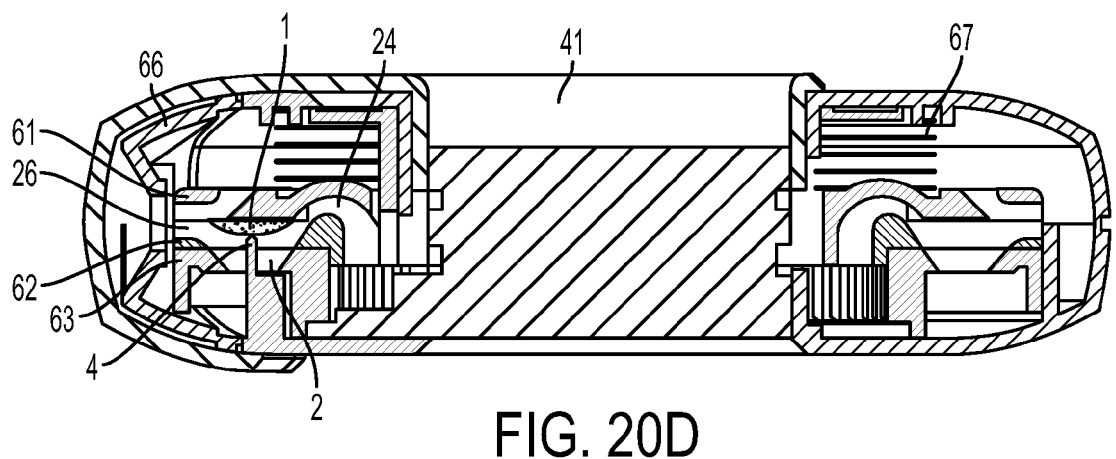
FIG. 20d shows a cross sectional view of the FIG. 20a embodiment with a dose chamber positioned in engagement with the punch.
Figure 22A:
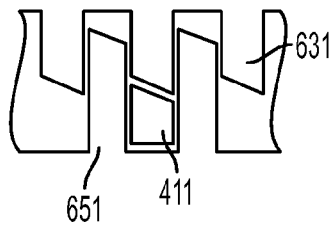
FIGS. 22a-22d show schematic views of portions of the lower housing and lower enclosure of the FIG. 20a embodiment in connection with movement of the lower housing relative to the lower enclosure.
Figure 22B:
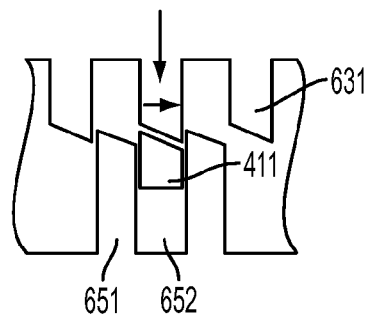
Figure 22C:
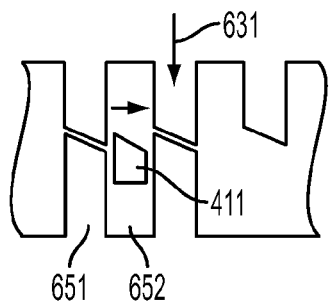
Figure 22D:
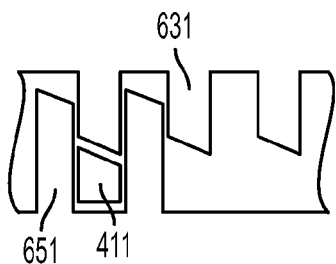

The mechanism that rotates the cassette to sequentially ready each dose chamber for delivery comprises various features on each of the actuation button 41, the lower housing 63 of the cassette, and the lower enclosure 65 of the delivery device. To cause rotation, the actuation button 41 includes three protrusions 411 that are ratcheted between slots that lie between teeth 651 in the lower enclosure half 65 through interaction with teeth 631 that extend from the lower cassette housing 63. It is to be appreciated that other numbers of protrusions may also be used. With the actuation button located, as shown in FIG. 20d, the protrusions of the button are nested in slots of the lower enclosure 65. Movement of the actuation button 41 toward the upper enclosure 61 causes the actuation button protrusions 411 to move upward, as shown in FIG. 22b. A spring 67 in the delivery device may resist motion of the cassette in this direction, causing a downward force on the cassette, as represented in FIGS. 22a-22d. Interaction between ramped surfaces on the protrusions 411 and the teeth 631 of the lower housing convert the downward force into a rotational force on the cassette. Once the protrusions are moved beyond the upper edge of the slots 652 of the lower enclosure, the cassette rotates with the ramped surface of the teeth sliding on a corresponding ramped surface on an upper surface of the lower teeth, until the teeth 631 of the lower cassette housing abut the protrusions 411, as shown in FIG. 22c. The position shown in FIG. 22c corresponds roughly to that represented in FIG. 20c, where the cassette is located at its upward most point of travel within the delivery device. Pushing the actuation button 41 in the opposite direction, causes the protrusion 411 to travel downward into the slot 652 between the teeth 651 of the lower enclosure, and the ramped surface on teeth 631 of the lower cassette housing then interacts with the ramped surfaces on teeth 652 of the lower enclosure to further rotate the cassette. It is to be appreciated that the above described mechanism is but one type of mechanism that may be used to raise and lower the cassette, and that others are also possible and are contemplated, such as mechanisms that uses a cam attached a movable mouthpiece that acts to rotate the cassette, and/or a lever, like the cover in the embodiment of FIGS. 20a-20d, that rotates or pivots to rotate the cassette. According to one embodiment, moving the cover shown in FIG. 20a, engages a cam to move the button/cassette upward to the position shown in FIG. 20c, thereby eliminating one step for a user to ready the device for dose delivery.

In the embodiment of FIGS. 20a-20d, movement of the actuation button in each direction causes the cassette to rotate only half of the distance required to index a dose chamber to be readied for dose delivery. For a multi-dose device having sixty doses, this may include 3 degrees of rotation. Actuation of the button in the opposite direction completes the process of readying the dose by rotating the cassette an additional 3 degrees.

Rotating the cassette, as described above, brings the mouthpiece 5 and air outlet of the delivery device sequentially into registration with the dose channel air outlet of a dose chamber that is to be opened, as shown in FIG. 20d. Additionally, movement of the cassette downwardly toward the lower enclosure half 65 brings the dose chamber into contact with the punch 1 to open the dose chamber, as described herein. When the cassette is positioned near the upper enclosure half 64, the air outlet of the mouthpiece is not registered with any dose chamber air outlets. Instead, a solid portion of the cassette blocks the mouthpiece opening, providing a visual indication that the device is not ready to dispense a dose.

The multi-dose device may also include a dose counter. The embodiment of FIGS. 20a-20d includes dose counter ring 68 that rotates with the cassette to sequentially show different numbers on the counter ring through a window 69 on the upper enclosure half. When the cassette is positioned as shown in FIG. 20c, the window 69 may show portions of two different dose numbers, or no dose number at all. According to other embodiments, however, a mechanism may be included in the device such that the counter ring 68 only indexes when a subsequent dose is readied for dispensation. Additionally or alternatively, other embodiments may include a counter wheel with numbers thereon that are punctured when a dose chamber is opened, thereby indicating that a particular number of doses have been used, or remain.

Figure 23:
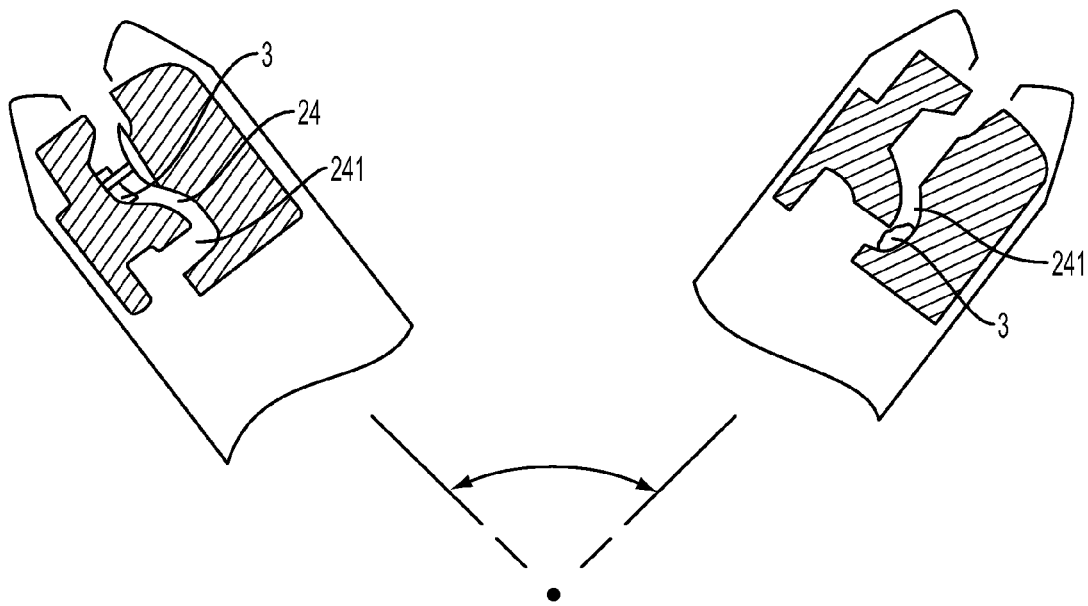
FIG. 23 shows an illustrative arrangement of the FIG. 20a embodiment in which a dose chamber inlet includes a feature to help trap dose.

Air pathways may be shaped to prevent the loss of dose, should a device be moved through a range of motions after a dose chamber has been opened but before the dose has been delivered. By way of example, as shown in FIGS. 20*c* and 20*d*, the air pathway includes a U-shaped bend 241 that is configured at an inner end of the dose chamber inlet 24 to catch any dose that may fall out of the dose chamber, at least through a particular range of motion. Dose that is caught in the U-shaped bend 241 will still be delivered to the user, as the dose still lies in the air pathway through which air will be drawn. This is illustrated in FIG. 23, where the multi-dose device is held in a first orientation when a dose chamber is opened, and then a second orientation for delivery of the dose.

According to some embodiments, a multidose device may include features that plug or impede the flow of air through air pathways other than that of the dose chamber that is in registration with the mouthpiece. By way of example, FIG. 20*a* shows the backside of the mouthpiece, which includes baffles 53 that prevent fluid communication with air pathways, other than that in registration. Additionally or alternatively, some embodiments may include plugs or other features that are positioned at the dose chamber air inlet of dose chamber adjacent to the one in registration. Preventing flow through adjacent dose chamber air pathways may help direct a greater amount of air flow through the dose chamber in registration, resulting in improved dose delivery.

Figure 24:
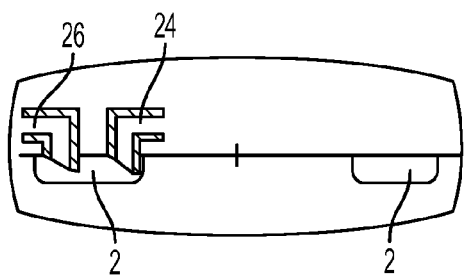
FIG. 24 shows an illustrative embodiment in which a dose chamber inlet and outlet pierce a dose chamber.

It is to be appreciated that while the multidose device of FIGS. 20*a*-20*d* is described herein with respect to a particular type of opening mechanism, that the structure and mechanisms of the multi-dose device may be used with other types of opening mechanism. FIG. 24 shows one example of such an embodiment a pair of hollow punches are moved through a barrier of each dose chamber to provide an air inlet channel 24 and an air outlet channel 26 for the delivery of a dose. In this embodiment, the punches are hollow, and include portions of the air flow pathway. It is to be appreciated that other embodiments may also use hollow punches, through which air may flow, as such features are not limited to devices like that shown in FIG. 24.

Figure 25:
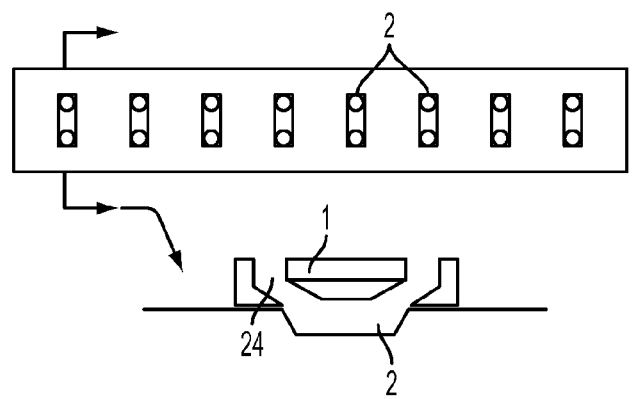
FIG. 25 shows an embodiment in which a plurality of dose chambers are arranged in a strip.

It is also to be appreciated that multi-dose devices may configured differently than the embodiment shown in FIGS. 20*a*-20*d*. By way of example, according to some embodiments, dose chambers may be arranged in a strip, as shown in FIG. 25. In this embodiment, each dose chamber includes an internally positioned cutter and features that form portions of air pathways. According to other embodiments, a multi-dose device may include a housing that holds individual dose chambers that may each be loaded into a common device for opening and dose delivery. FIG. 24 illustrates one type of relatively low cost device that may be used in such an embodiment may include an actuator that includes a living hinge. A first portion of the device may hold a dose chamber while a second portion of the device maybe folded about a living hinge to bring a punch into contact with dose chamber. It is to be appreciated that FIG. 24 represents but one variation of a multi-dose delivery device, and that others are contemplated.

According to other multi-dose embodiments, the cassette may be include a plurality of foil-on-foil dose chambers, rather than chambers formed from barrier material and more rigid plastic material, as in the embodiment of FIGS. 20*a*-20*d*. Such embodiments may prove to be less costly.

Delivery devices may also include multiple dose chambers that are opened to expose different doses to a common air pathway for delivery. For instance, some drugs that might be delivered include components that should not be mixed until the components are delivered to a user. In such instances, or for other types of combination therapies, two or more dose chambers may be opened to provide doses to a user at a common time, either through a common airway where the different doses are mixed prior to delivery, or through different air pathways.

Figure 26:
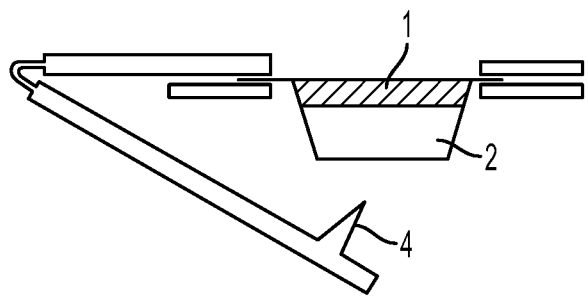
FIG. 26 shows an embodiment in which a punch is attached to a dose chamber.

FIG. 26 shows an embodiment in which a punch 4 is mounted via a living hinge to a dose chamber 2. The punch 4 may be moved via the living hinge to contact the cutter 1 and open the dose chamber 2. Such an arrangement may be substituted for the punch arrangement in any one of the suitable embodiments described herein.

Figure 27:
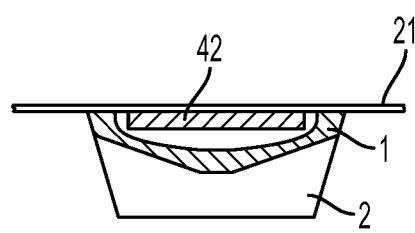
FIG. 27 shows an embodiment in which a cutter is arranged to accommodate a dessicant in the dose chamber.
Figure 28:
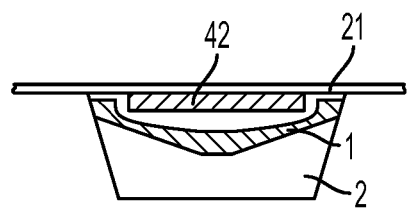
FIG. 28 shows an embodiment in which a cutter is arranged to accommodate a dessicant in the dose chamber and includes an air pathway.

According to some embodiments, desiccant materials may be incorporated into a dose chamber to absorb any moisture that might enter the chamber. FIG. 27 shows one embodiment where desiccant material 42 is positioned inside of a pocket that is formed between the upper foil layer and the cutter 1. The cutter may be made of a material, such as plastic, that is somewhat permeable so that any moisture may pass move from the chamber and toward the desiccant. As shown in the embodiment of FIG. 28, passageways may be included within the cutter (e.g., near the top barrier layer 21) to allow moisture to reach the desiccant more readily. As shown, the passageways are positioned to open near the interface between the upper and lower foil layers 21, 22, which is the most likely place where moisture may enter the dose chamber. The passageways are additionally positioned between the cutter and the foil to prevent the dose from coming in direct contact with the desiccant, which may be desirable for some applications.

Figure 31A:
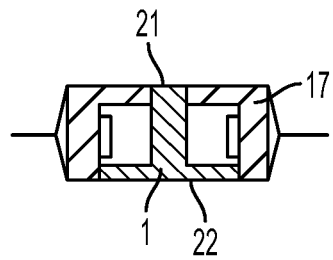
FIGS. 31a and 31b show an embodiment in which a dose chamber includes a cutter arranged within a structure that helps guide movement of the cutter.
Figure 31B:
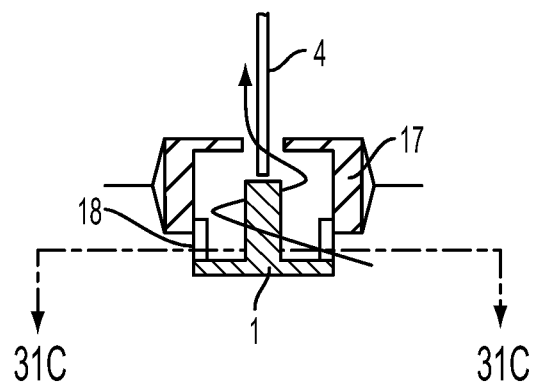
Figure 31C:
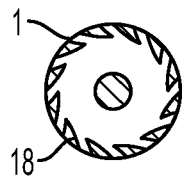
FIG. 31c shows a cross sectional view of the FIG. 31b cutter along the line 31c-31c.
Figure 31D:
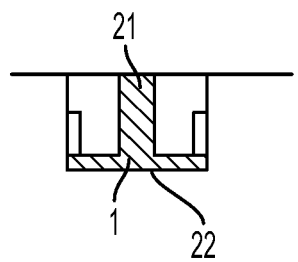
FIG. 31d shows an alternate embodiment of FIGS. 31a and 31b without the structure in the dose chamber.

FIGS. 29*a* and 29*b* show an embodiment in which the cutter 1 has a hinge 15. The punch 4 includes a pair of prongs that contact the cutter 1 so that the cutter 1 moves upwardly and the opposite ends of the cutter 1 fold around a portion of a housing 6 or other receiving structure. FIGS. 30*a* and 30*b* show a similar arrangement except that the hinge 15 is replaced by a gap 16 or void in the cutter 1. FIG. 30*c* shows another embodiment in which the cutter 1 is arranged to rotate about an axis near one side of the cutter 1. Thus, when the punch 4 pushes the cutter 1 upwardly, the cutter 1 rotates to open the dose chamber 2. FIGS. 31*a* and 31*b* show another embodiment in which a dose chamber 2 includes a cutter 1 that is movable within a structure 17 that is also located within a pair of barrier layers 21, 22. The dose chamber 2 may be opened by a punch 4 pushing on the cutter 1, which causes the cutter 1 to pierce the lower foil layer 22 and open the dose chamber 2. Movement of the cutter 1 may be guided by interaction of walls 18 on the cutter 1 with the structure 17. FIG. 31*c* shows an optional arrangement for the walls 18 of the cutter 1 in which the walls 18 induce a rotary or spiral flow of air through the dose chamber 2 (see FIG. 31*b*). FIG. 31*d* shows an arrangement in which the cutter 1 of FIG. 31*c* is used in a dose chamber 2 that includes only foil layers 21, 22 and no structure 17.

FIG. 32 shows a side view and FIG. 33 an exploded view of another dose delivery device that incorporates one or more aspects of the invention. In this embodiment, the delivery device includes a mouthpiece 5 with a mouthpiece outlet 52 near a top of the device. A lower housing 63 supports the mouthpiece 5 and includes optional ribs or grooves to help improve a user's grip on the device. As is described more below, the mouthpiece 5 may be moved relative to the lower housing 63, e.g., by rotation and/or upward movement away from the lower housing 63. In the exploded view of FIG. 33, it can be seen that the lower housing 63 is arranged to receive an upper housing 61 and a dose chamber 2. The upper housing 61 includes air flow path features including one or more bypass channels 23, one or more dose chamber air inlet channels 24, an air inlet 25 arranged around a periphery of the upper housing 61 and others not shown in FIG. 33. The mouthpiece 5 engages with the upper and lower housings 61, 63 at least in part by a cam surface 81. As will be understood more from the following, rotation of the mouthpiece 5 about a vertical axis relative to the upper and lower housings 61, 63 causes the engagement of the mouthpiece 5 at the cam surface 81 to move upward/downward based on the rotary position of the mouthpiece 5. It will be understood that other types of engagement, such as threaded engagement, may be used to cause axial movement of the mouthpiece 5 in response to rotation of the mouthpiece. Alternately, the mouthpiece need not rotate at all relative to the housings 61, 63, but instead may only move linearly relative to the housings 61, 63. The inlet end of the mouthpiece 5 includes a puller 7 that is arranged to engage with a cutter 1 of the dose chamber 2 to pull the cutter 1 away from the dose chamber 2 so as to open the chamber for introduction of a dose 3 into the air flow path of the device, e.g., an air path of the mouthpiece 5. In accordance with an aspect of the invention, the puller 7 may move the cutter 1 in a single direction away from the dose chamber 2 when opening the dose chamber 2. That is, rather than moving the cutter 1 towards the dose chamber (e.g., to break the cutter 1 free of the dose chamber) followed by movement away from the dose chamber, the puller 7 may engage the cutter 1 and then move the cutter 1 away from the dose chamber 2. Of course, the movement in a single direction may incorporate either linear motion of the cutter 1 (e.g., up/down motion) and/or rotary motion of the cutter (e.g., rotational motion around a vertical axis due to rotation of the mouthpiece). Thus, reference to movement in a single direction refers to the fact that the cutter 1 moves only away (rather than toward) the dose chamber 2 during the opening process.

FIGS. 34-36 show the delivery device in different stages of operation, i.e., different positions of the mouthpiece 5 relative to the upper and lower housings 61, 63. In FIG. 34, the mouthpiece 5 is in an initial position before the dose chamber has been opened. The puller 7 is located above the dose chamber 2 and the cutter 1. Rotation of the mouthpiece 5 causes the mouthpiece 5 to move downwardly toward the housings 61, 63 as shown in FIG. 35. The puller 7 moves to engage the cutter 1 in a suitable way, such as by inserting a pin near the center of the puller 7 into a corresponding groove in the cutter 1 and/or by engaging an annular ring near a periphery of the puller 7 with the outer periphery of the cutter 1. As discussed above, although the term "cutter" is used to refer to an element associated with the dose chamber 2 that functions to open the chamber 2, the cutter 1 need not necessarily cut or otherwise pierce any barrier layer of the dose chamber 2. Instead, the cutter 1 may function in other ways to open the dose chamber 2 to expose the dose for introduction into the device air path. For example, the dose in the embodiment of FIG. 1a is constrained to the dose chamber 2 by the cutter 1, not by the top layer of barrier material 21. While the barrier layer 21 may help seal the dose chamber closed, the dose chamber is actually opened, and the dose exposed for introduction into an air flow path of the device, by movement of the cutter 1 away from the lower portion of the dose chamber 2. It is for this reason that the cutter 1 is, in at least some embodiments (including this one), referred to as a disc element where the cutter 1 has a disc shape, e.g., a relatively flat element having a circular, diamond, oval, or other shape as discussed above. In this embodiment, the disc element 1 is substantially rigid and is exposed to the dose 3 at a lower side of the element 1. Thus, the element 1 can help constrain the dose to a desired area of the dose chamber 2 and expose the dose when moved to open the dose chamber 2, like several of the embodiments discuss above.

Engagement of the puller 7 with the cutter 1 (or disc element) causes the cutter 1 to "stick" to the puller 7 so that when the puller 7 is moved upwardly again in response to rotation of the mouthpiece 5, the cutter 1 moves upwardly and away from the dose chamber 2, allowing the dose to be introduced into the device air flow path. This upward movement may cause the cutter 1 to move any barrier layer (if present) above the cutter 1 to be pushed aside and/or cut away from the dose chamber 2. Also, the puller 7 may include an edge that cuts a portion of a foil barrier layer on top of the disc element 1 (if present) as the puller 7 moves toward the disc element 1 for engagement with the disc element 1. Opening of the dose chamber 2 can then be completed by the puller 7 lifting the disc element 1 from the dose chamber 2. It should be appreciated that the function of the puller 7 may be used in other embodiments described herein, including the embodiment of FIG. 20a. For example, the punch 4 of the FIG. 20a embodiment may be replaced by a puller 7 (or a plurality of pullers 7, one for each dose chamber) that is located above the dose chamber (i.e., a side opposite the location of the punch 4). An actuation button or other element may move the puller(s) into engagement with a respective cutter 1, and pull the cutter from the dose chamber to open the chamber.

As air is drawn from the mouthpiece outlet 52 with the dose chamber 2 open, air enters the device at the inlet 25, i.e., into a space between the upper and lower housings 61, 63 around the periphery of the upper housing 61. A portion of the air may flow into the dose chamber inlet(s) 24, while other portions may flow through the bypass(es) 23 and into the inlet 51 of the mouthpiece. Air passing into the dose chamber inlet 24 may enter the dose chamber 2 to pick up a portion of the dose 3 and exit the chamber 2 for flow to the inlet of the mouthpiece 51.

One feature of the device in FIGS. 32-36 is that the dose chamber 2 may be re-closed by rotation of the mouthpiece 5. That is, since the cutter 1 is substantially rigid and arranged to contact a lower portion of the dose chamber 2 so as to close the chamber at a contact area between the cutter 1 and the lower portion of the dose chamber 2 (e.g., at a lower periphery of the cutter 1), the cutter 1 may be moved to the closed position to trap any remaining dose 3 in the chamber 2 for later use and/or disposal. Alternately, the device could be arranged so that the dose chamber cannot be reclosed, e.g., to ensure that the device is used only a single time.

FIGS. 37 and 38 show cross sectional views depicting the arrangement of the inlet end of the mouthpiece and the dose chamber inlet 24 in this embodiment. FIG. 37 shows the vanes of a flow straightener 28 near the inlet 51 of the mouthpiece 5. Also shown are tabs on the mouthpiece 5 that engage with slots or grooves (e.g., the cam surface 81) in the upper housing 61. FIG. 38 shows that the dose chamber inlet 24 includes a plurality of passageways that lead to the dose chamber 2. The passageways are arranged to induce a swirling or circular flow at the dose chamber 2 and may persist toward the inlet 51 of the mouthpiece. Also, the bypasses 23 additionally induce a swirling flow near the inlet 51 of the mouthpiece. While the passageways in this embodiment are formed in the housing 61, the passageways could be formed in a portion of the mouthpiece and/or other portions of the device.

Figure 39:
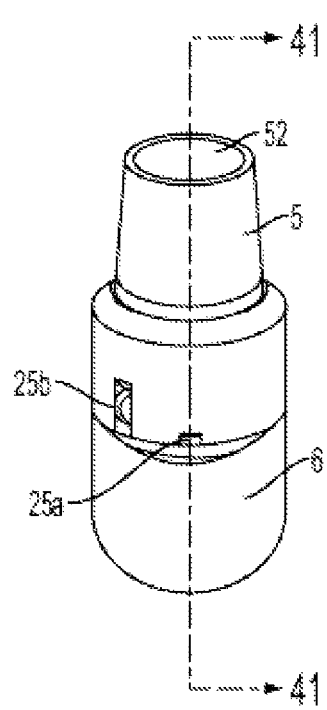
FIG. 39 shows a front view of another illustrative embodiment of a dose delivery device.
Figure 40:
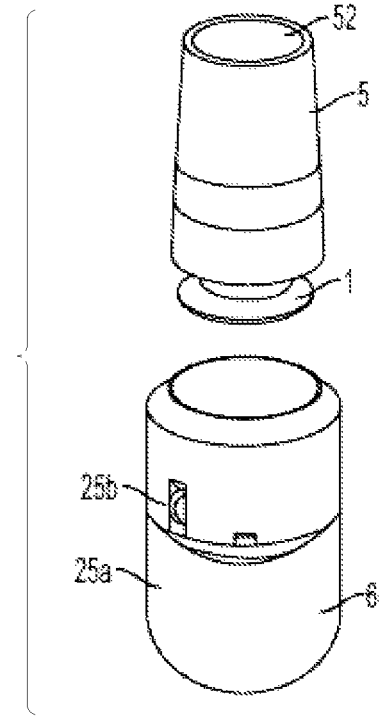
FIG. 40 shows an exploded view of the FIG. 39 embodiment.
Figure 41:
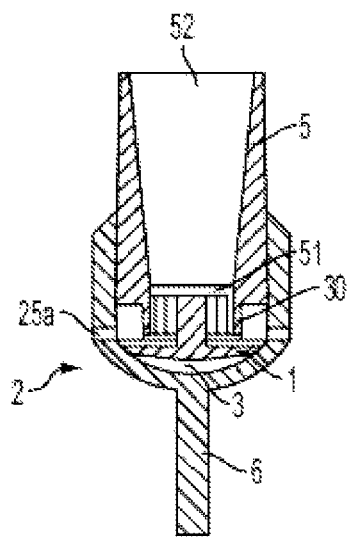
FIGS. 41 and 42 show cross sectional views along the line 41-41 in FIG. 39 with the mouthpiece in different positions.
Figure 42:
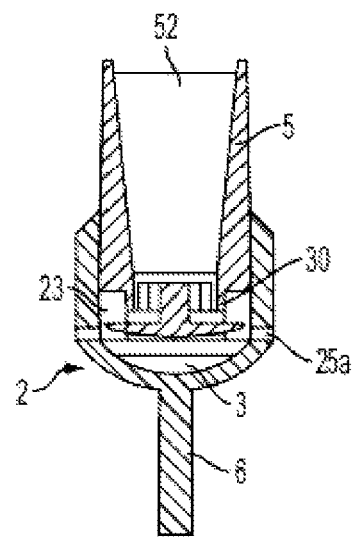

FIG. 39 shows a side view and FIG. 40 an exploded view of another dose delivery device that incorporates one or more aspects of the invention. In this embodiment, a mouthpiece 5 is received by a housing 6 that has a recess to accept the inlet end of the mouthpiece 5. The inlet end of the mouthpiece 5 carries a disc element 1 that is fixed relative to the mouthpiece 5. As can be seen in the cross sectional view of FIG. 41, the housing 6 includes a depression that functions as part of a dose chamber 2 together with the disc element 1. That is, a dose 3 may be placed in the depression of the housing 6 and the mouthpiece 5 inserted into the housing 6 so that the disc element 1 covers the dose 3 and closes the dose chamber 2. The mouthpiece 5 is movable axially (e.g., in a vertical direction) relative to the housing 6 so that the disc element 1 can be moved away from the depression of the housing 6 and the dose 3 so that the dose chamber 2 is opened and the dose exposed for introduction into an air pathway of the device. With the mouthpiece 5 and disc element 1 moved to open the dose chamber 2 as shown in FIG. 42, air may enter the inlet 25a and pass through a dose chamber inlet 24 to the dose chamber 2 to entrain dose 3. In addition, air may enter the inlet 25b, which provides air to a bypass 23, e.g., to allow air to flow from the inlet 25b to the inlet 51 of the mouthpiece 5 without passing through the dose chamber 2. Thus, the air from the bypass 23 and the dose chamber inlet 24/dose chamber 2 may be combined in the mouthpiece 5 for exit at the outlet 52. The lower end of the mouthpiece 5 may include a lip obstacle 30 similar to that discussed above with reference to FIG. 14 that helps ensure that suitably sized dose particles enter the mouthpiece inlet 51 while larger particles remain behind.

Figure 43:
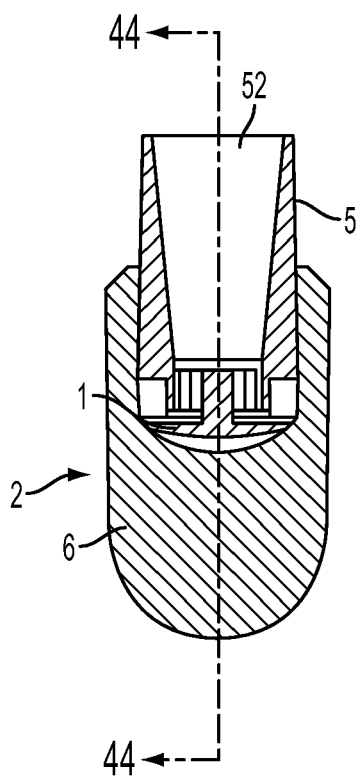
FIG. 43 shows a cross sectional view of the FIG. 39 embodiment along the line 43-43 in FIG. 44.
Figure 44:
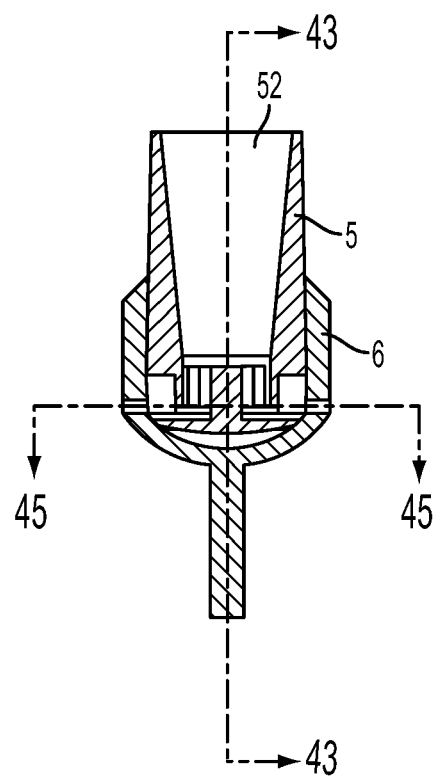
FIG. 44 shows a cross sectional view along the line 44-44 in FIG. 43.
Figure 45:
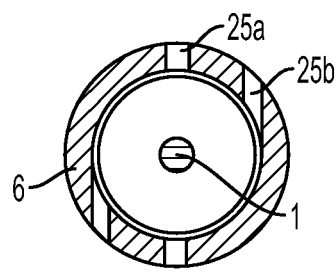
FIG. 45 shows a cross sectional view along the line 45-45 in FIG. 44.

The closure provided by the disc element 1 for the dose chamber 2 may or may not provide a hermetic seal at the dose chamber 2, but the disc element 1 generally provides a seal that restrains dose 3 from exiting the dose chamber 2 until the disc element 1 is moved to the open position. The mouthpiece 5 and housing 6 may include a detent or other feature that helps to keep the mouthpiece in the open and closed positions. Thus, the detent may tend to keep the disc element 1 and mouthpiece 5 in the closed position of FIG. 41 until a user exerts suitable force on the mouthpiece 5 to move to the open position of FIG. 42. Once in the open position, the detent may keep the mouthpiece in that position until, again, suitable force is exerted to move the mouthpiece 5 and disc element to the closed position. The mouthpiece and housing 6 may be engaged in other suitable ways, such as by a threaded engagement or cam arrangement (so rotation of the mouthpiece 5 relative to the housing 6 causes not only relative rotation but axial movement of the mouthpiece 5 like that in FIGS. 32-38. As can be appreciated from FIGS. 43 and 44, the housing 6 may include a tab like projection at the lower end of the housing 6, e.g., for gripping between a thumb and forefinger of a user. This may allow a user to grasp the mouthpiece 5 with another hand and pull the mouthpiece 5 upwardly relative to the housing 6 (or rotate the mouthpiece 5 or otherwise cause relative movement). As shown in FIG. 45, the inlets 25a that provide air to the dose chamber inlet 24 may be directed to a center of the dose chamber 2, whereas the inlets 25b that provide air to the bypass 23 may induce a swirling or spiral flow. Opposing air flow from the inlets 25a in the dose chamber 2 may induce turbulence that helps dose to be entrained in the air flow, while the spiral flow induced by the inlets 25b may help remove the entrained dose/air from the dose chamber 2. Of course, the air flow induced in the device may be arranged in other suitable ways.

It is to be appreciated that the embodiments illustrated herein are merely representative embodiments of the various inventions, and that modifications may be made without departing from the spirit of the invention. By way of example, air pathways may be modified to have different shapes or features, or be located in various different parts of the dose deliver device for manufacturing or other reasons. For example, the housings 6, 61, 63 could be made to be received into the lower end of the mouthpiece 5 rather than have a portion of the mouthpiece received in the housings as in FIGS. 32-45. Some embodiments like that of FIGS. 1*a*-3*b* may be modified to include a right angle outlet similar to FIG. 14. Additionally or alternatively, some embodiments (like those in FIGS. 32-45) may be constructed with a device that pulls a cutter away from a dose chamber to rupture a barrier, such as a hook or other puller, rather than a punch that pushes a cutter. In such embodiments, a puller may engage and interlock the cutter (as in FIGS. 32-38), or may permanently be attached to the cutter (as in FIGS. 39-45). Other potential modifications are also contemplated, even though not explicitly described herein.

In some embodiments, the devices, systems and methods may be free of secondary packaging to facilitate rapid and easy delivery of the drug when the drug needs to be delivered as fast as possible under a stressful circumstance, such as in an emergency situation. However, some embodiments, such as that in FIGS. 39-45 may have the entire device enclosed in a bag, e.g., of barrier layer foil or other material, to help preserve the dose 3 or otherwise provide the dose 3 with suitable conditions for storage.

Embodiments described herein may be configured for passive or active applications, or a combination of passive and active fluid administration. For example, each of the embodiments described herein may include use of a compressed fluid to assist in dispersing the drug.

The devices and systems described herein may be integrated into a wide variety of delivery configurations including, for example, a single-dose and multi-dose applications, in either active, passive, or active/passive applications. In addition, the devices, systems and methods may be applied to combination dose configurations and therapies.

The devices, systems and methods described herein may be used to deliver materials, other than a drug/medicament, to the body. The materials may be delivered through the mouth and/or nose and into the oral cavity, nasal cavity, and/or to the lungs. Materials that are intended to be delivered into the oral cavity include, for example, nutritional compositions (such as sugars, candy, food, vitamins, and quick energy supplements in liquid and/or powder (e.g., nanoparticles) form) and non-nutritional compositions (such as flavorants (e.g., esters)). Other materials that may be delivered into the oral cavity include those used for oral hygiene and dental treatment (e.g., breath fresheners, fluoride treatments, teeth whiteners, anti-bacterial compositions, mouthwashes). Drugs and related compositions (such as anesthetics, therapeutic markers) may also be delivered into the oral cavity. Materials that the may be inhaled into the lungs include, for example, drugs (e.g., for treating asthma, bronchitis, diabetes, pneumonia) and therapeutic markers (such as dyes, scanning agents, radio labeling or tagging agents, UV labeling agents, contrasts agents in liquid and/or powder (e.g., nanoparticles) form). In this respect, it is to be appreciated that any of the above materials may be used in the devices, systems, and methods described herein in place of drug(s)/medicaments. It is also to be appreciated that the terms “drug” and “medicament” are used interchangeable herein, and include any of the foregoing compositions and any others, whether in powder, liquid or other form, that may be delivered to a human or animal for therapeutic, diagnostic, or other effect. In certain aspects, the delivery device is configured for use with other entranceways into a human or animal body, whether naturally formed or created otherwise, and with aspects of the human or animal body other than the respiratory system. Although the embodiments described incorporate air as the fluid for delivering the medicament, other fluids are contemplated as should be apparent to one of skill in the art.

Although embodiments are described as including a “mouthpiece,” it should be understood that a “mouthpiece” as used herein refers to an element that is downstream of a dose chamber and is intended to deliver an air/dose combination toward an ultimate outlet located at or near a user's mouth, nose or other receiving area. Thus, a "mouthpiece" need not necessarily be intended for contact with a human mouth. For example, a mouthpiece may be intended for use near a mouth, such as where a user holds the device spaced from the mouth and inhales dose/air emitted from the device outlet. In another embodiment, a mouthpiece may be intended for use with another element that is engaged with the mouthpiece (e.g., at the mouthpiece outlet 52) and is intended for contact with the user's mouth. In one example, a disposable or reusable sleeve or other conduit may be connected to the mouthpiece outlet 52 and provide an extension of the air path of the device beyond the mouthpiece outlet 52. The fact that a dose delivery device is used, or intended for use, with such a sleeve would not render the air flow component downstream of the dose chamber (i.e., the "mouthpiece") that conducts an air/dose combination not a "mouthpiece" as used herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A dose delivery device, comprising:
   a mouthpiece having an inlet at a first end, an outlet at a second end, and a mouthpiece air path extending between the inlet and the outlet;
   a dose chamber holding a dose and having an opening;
   a cutter inside the dose chamber arranged to move between a closed position and an open position in which the dose chamber is opened to permit introduction of the dose into the air path;
   a barrier layer covering the opening of the dose chamber; and
   a puller arranged to engage with the cutter while the cutter is in the closed position and move the cutter from the closed position to the open position such that the barrier layer is cut to open the dose chamber.

2. The device of claim 1, wherein the puller includes an edge that cuts a portion of the barrier layer near the cutter as the puller moves toward the cutter for engagement with the cutter.

3. The device of claim 1, further comprising:
   a housing that engages a portion of the mouthpiece such that the mouthpiece is movable relative to the housing.

4. The device of claim 3, wherein the cutter is arranged to move from the closed position to the open position with movement of the mouthpiece relative to the housing.

5. The device of claim 1, wherein the cutter directs air to flow into the dose chamber when the cutter is in the open position.

6. The device of claim 1, further comprising:
   a housing that engages the first end of the mouthpiece such that the mouthpiece is movable relative to the housing, and wherein the mouthpiece air path extending from the inlet to the outlet extends along an axis, and wherein the mouthpiece is movable along the axis relative to the housing.

7. The device of claim 6, wherein the cutter is arranged to move from the closed position to the open position with movement of the mouthpiece relative to the housing.

8. The device of claim 1, wherein the puller is configured to interlock with the cutter.

9. The device of claim 1, wherein the cutter is configured to cut through the barrier layer.

10. The device of claim 1, wherein the cutter includes a disc element.

11. The device of claim 1, wherein the cutter has a shape that conforms to the opening of the dose chamber.

12. The device of claim 1, further comprising a spring configured to move the puller and the cutter engaged with the puller to open the dose chamber.

13. The device of claim 1, further comprising a cam mechanism configured to cause the puller to move toward the cutter in response to rotation.

14. The device of claim 1, further comprising multiple dose chambers.

15. The device of claim 14, further comprising an indexing mechanism configured to index an opening of each of the chambers into registration with the mouthpiece air path.

16. The device of claim 1 wherein the cutter constrains the dose to a particular area of the dose chamber.

* * * * *